(12) United States Patent
Gotlib et al.

(10) Patent No.: US 7,848,935 B2
(45) Date of Patent: Dec. 7, 2010

(54) MEDICAL INFORMATION EVENT MANAGER

(75) Inventors: Phyllis Gotlib, Tel Aviv (IL); Ido Schoenberg, Tel Aviv (IL); Roy Schoenberg, Tel Aviv (IL)

(73) Assignee: I.M.D. Soft Ltd., Needham, MA (US)

( * ) Notice: Subject to any disclaimer, the term of this patent is extended or adjusted under 35 U.S.C. 154(b) by 1409 days.

(21) Appl. No.: 10/355,435

(22) Filed: Jan. 31, 2003

(65) Prior Publication Data

US 2004/0152952 A1 Aug. 5, 2004

(51) Int. Cl.
G06Q 10/00 (2006.01)
G06Q 50/00 (2006.01)
(52) U.S. Cl. .......................................................... 705/2
(58) Field of Classification Search ................. 705/2–4; 704/9; 707/1
See application file for complete search history.

(56) References Cited

U.S. PATENT DOCUMENTS

| | | | |
|---|---|---|---|
| 3,646,606 A | 2/1972 | Buxton et al. |
| 4,489,387 A | 12/1984 | Lamb et al. |
| 4,709,331 A | 11/1987 | Barkett et al. |
| 4,719,338 A | 1/1988 | Avery et al. |
| 4,731,725 A | 3/1988 | Suto et al. |
| 4,736,322 A | 4/1988 | Clifford |
| 4,807,170 A | 2/1989 | Kulli et al. |
| 4,835,372 A | 5/1989 | Gombrich et al. |
| 4,838,275 A | 6/1989 | Lee |
| 4,852,570 A | 8/1989 | Levine |
| 4,878,175 A | 10/1989 | Norden-Paul et al. |
| 5,065,315 A | 11/1991 | Garcia |
| 5,199,439 A | 4/1993 | Zimmerman et al. |
| 5,255,187 A | 10/1993 | Sorensen |
| 5,262,944 A | 11/1993 | Weisner et al. |
| 5,301,105 A | 4/1994 | Cummings, Jr. |
| 5,307,263 A | 4/1994 | Brown |

(Continued)

FOREIGN PATENT DOCUMENTS

WO  WO 98/29790  7/1998

(Continued)

OTHER PUBLICATIONS

Hosseinzadeh, Abolfazl, "A Rule-Based System for Vital Sign Monitoring in Intensive Care", Department of Electrical Engineering, McGill University, Montreal; Nov. 1993.

(Continued)

*Primary Examiner*—Gerald J. O'Connor
*Assistant Examiner*—Linh Michelle Le
(74) *Attorney, Agent, or Firm*—Fish & Richardson P.C.

(57) ABSTRACT

An event management system and method detects the occurrence of events as a function, at least in part, of information and data gathered from monitoring one or more patients with a medical information system. Event detection processes can be defined and then triggered to cover any of a variety of circumstances. For instance, event detection processes can be defined that, when triggered, indicate that a certain patient (or patients) would make a suitable candidate for that clinical trial, a patient is a candidate for a certain type of treatment, or hospital resources are being utilized in a certain manner. That is, such events may relate to the efficiency or inefficiency in use of certain resources, or such events may concern usage under certain circumstances.

34 Claims, 10 Drawing Sheets

U.S. PATENT DOCUMENTS

| | | | |
|---|---|---|---|
| 5,321,800 A | 6/1994 | Lesser | |
| 5,335,346 A | 8/1994 | Fabbio | |
| 5,348,008 A | 9/1994 | Bornn et al. | |
| 5,398,300 A | 3/1995 | Levey | |
| 5,404,292 A | 4/1995 | Hendrickson | |
| 5,447,164 A | 9/1995 | Shaya et al. | |
| 5,482,050 A | 1/1996 | Smokoff et al. | |
| 5,544,649 A | 8/1996 | David et al. | |
| 5,544,661 A | 8/1996 | Davis et al. | |
| 5,572,422 A | 11/1996 | Nematbakhsh et al. | |
| 5,574,828 A | 11/1996 | Hayward et al. | |
| 5,576,952 A | 11/1996 | Stutman et al. | |
| 5,594,638 A | 1/1997 | Iliff | |
| 5,619,991 A | 4/1997 | Sloane | |
| 5,630,664 A | 5/1997 | Farrelly | |
| 5,678,562 A | 10/1997 | Sellers | |
| 5,687,717 A | 11/1997 | Halpern et al. | |
| 5,701,894 A | 12/1997 | Cherry et al. | |
| 5,704,350 A | 1/1998 | Williams, III | |
| 5,715,451 A | 2/1998 | Marlin | |
| 5,724,580 A | 3/1998 | Levin et al. | |
| 5,729,479 A | 3/1998 | Golan | |
| 5,752,621 A | 5/1998 | Passamante | |
| 5,772,585 A | 6/1998 | Lavin et al. | |
| 5,772,601 A | 6/1998 | Oka et al. | |
| 5,781,442 A | 7/1998 | Engleson et al. | |
| 5,794,208 A | 8/1998 | Goltra | |
| 5,801,755 A | 9/1998 | Echerer | |
| 5,822,544 A | 10/1998 | Chaco et al. | |
| 5,823,948 A | 10/1998 | Ross, Jr. et al. | |
| 5,830,150 A | 11/1998 | Palmer et al. | |
| 5,832,450 A | 11/1998 | Myers et al. | |
| 5,839,438 A | 11/1998 | Graettinger et al. | |
| 5,842,976 A | 12/1998 | Williamson | |
| 5,842,978 A | 12/1998 | Levy | |
| 5,845,255 A | 12/1998 | Mayaud | |
| 5,860,918 A | 1/1999 | Schradi et al. | |
| 5,867,821 A | 2/1999 | Ballantyne et al. | |
| 5,868,669 A | 2/1999 | Iliff | |
| 5,899,855 A | 5/1999 | Brown | |
| 5,912,656 A | 6/1999 | Tham et al. | |
| 5,921,920 A | 7/1999 | Marshall et al. | |
| 5,924,074 A | 7/1999 | Evans | |
| 5,940,815 A | 8/1999 | Maeda et al. | |
| 5,942,986 A | 8/1999 | Shabot et al. | |
| 5,956,689 A | 9/1999 | Everhart, III | |
| 5,970,463 A | 10/1999 | Cave et al. | |
| 5,987,519 A | 11/1999 | Peifer et al. | |
| 5,997,476 A | 12/1999 | Brown | |
| 6,024,699 A | 2/2000 | Surwit et al. | |
| 6,047,259 A | 4/2000 | Campbell et al. | |
| 6,061,657 A | 5/2000 | Whiting-O'Keefe | |
| 6,093,146 A | 7/2000 | Filangeri | |
| 6,101,478 A | 8/2000 | Brown | |
| 6,102,856 A | 8/2000 | Groff et al. | |
| 6,112,182 A | 8/2000 | Akers et al. | |
| 6,154,668 A | 11/2000 | Pedersen et al. | |
| 6,168,563 B1 | 1/2001 | Brown | |
| 6,206,829 B1 | 3/2001 | Iliff | |
| 6,215,403 B1 | 4/2001 | Chan et al. | |
| 6,225,901 B1 | 5/2001 | Kail, IV | |
| 6,230,142 B1 | 5/2001 | Benigno et al. | |
| 6,233,581 B1 | 5/2001 | Rambaud et al. | |
| 6,234,964 B1 | 5/2001 | Iliff | |
| 6,238,338 B1 | 5/2001 | DeLuca et al. | |
| 6,245,013 B1 | 6/2001 | Minoz et al. | |
| 6,254,536 B1 | 7/2001 | Devito | |
| 6,278,999 B1 | 8/2001 | Knapp | |
| 6,283,761 B1 | 9/2001 | Joao | |
| 6,292,698 B1 | 9/2001 | Duffin et al. | |
| 6,304,788 B1 | 10/2001 | Eady et al. | |
| 6,315,719 B1 | 11/2001 | Rode et al. | |
| 6,322,502 B1 | 11/2001 | Schoenberg et al. | 600/300 |
| 6,363,393 B1 | 3/2002 | Ribitky | |
| 6,364,834 B1 | 4/2002 | Reuss et al. | |
| 6,381,576 B1 | 4/2002 | Gilbert | |
| 6,385,589 B1 | 5/2002 | Trusheim et al. | |
| 6,398,728 B1 | 6/2002 | Bardy | |
| 6,413,224 B1 | 7/2002 | Ogura et al. | |
| 6,442,433 B1 | 8/2002 | Linberg | |
| 6,463,320 B1 | 10/2002 | Xue et al. | |
| 6,658,276 B2 | 12/2003 | Kianl et al. | |
| 6,700,028 B2 | 3/2004 | Dyroff | |
| 6,748,353 B1* | 6/2004 | Iliff | 704/9 |
| 6,804,558 B2 | 10/2004 | Haller et al. | |
| 6,804,656 B1 | 10/2004 | Rosenfeld et al. | |
| 6,893,396 B2 | 5/2005 | Schulze et al. | |
| 6,941,271 B1 | 9/2005 | Soong | |
| 7,039,878 B2 | 5/2006 | Auer et al. | |
| 7,374,535 B2 | 5/2008 | Schoenberg et al. | |
| 2002/0087355 A1* | 7/2002 | Rowlandson | 705/2 |
| 2002/0099273 A1 | 7/2002 | Bocionek et al. | |
| 2002/0173988 A1 | 11/2002 | Dang | |
| 2002/0177758 A1 | 11/2002 | Schoenberg et al. | |
| 2002/0177759 A1 | 11/2002 | Schoenberg et al. | |
| 2002/0187483 A1 | 12/2002 | Hoffman et al. | |
| 2003/0036687 A1 | 2/2003 | Schoenberg | |
| 2003/0163351 A1 | 8/2003 | Brown et al. | |
| 2004/0111296 A1 | 6/2004 | Rosenfeld | |
| 2004/0111297 A1 | 6/2004 | Schoenberg | |
| 2004/0111298 A1 | 6/2004 | Schoenberg | |
| 2004/0111622 A1 | 6/2004 | Schoenberg | |
| 2004/0152952 A1 | 8/2004 | Gotlib et al. | |
| 2004/0153343 A1 | 8/2004 | Gotlib et al. | |
| 2004/0225629 A1 | 11/2004 | Eder | |
| 2005/0125256 A1 | 6/2005 | Schoenberg et al. | |
| 2005/0256815 A1 | 11/2005 | Reeve et al. | |
| 2006/0004610 A1 | 1/2006 | David | |
| 2008/0208618 A1 | 8/2008 | Schoenberg et al. | |

FOREIGN PATENT DOCUMENTS

| | | |
|---|---|---|
| WO | WO 99/13766 | 3/1999 |
| WO | WO 00/79466 A2 | 12/2000 |
| WO | WO 2005/067675 A2 | 7/2005 |

OTHER PUBLICATIONS

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modelling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgy, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." *J. Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazurta, Jose, "Monitoring in Pediatric Intensive Care." *Indian J. Pediatrics*, vol. 60, 1993: 55-65.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems." *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical Monitoring*, vol. 10, No. 3, May 1994: 178-180.

Kohane, I. S. et al., "Hypothesis-Driven Data Abstraction with Trend Templates." In Symposium on Computer Applications in Medical Care, Oct. 30-Nov. 3, 1993, Washington, DC; pp. 444-448.

Koski, E. M. J. et al., "A Knowledge-Based Alarm System for Monitoring Cardiac Operated Patients—Assessment of Clinical Performance." *International J. Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International I Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 38, No. 5, Oct. 1993: 400-405.

M. de Beer, N. A. et al., "Clinical Evaluation of a Method for Automatic Detection and Removal of Artifacts in Auditory Evoked Potential Monitoring." *J. Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." *J. Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 21, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm " In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J. Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L.. "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (Paper on CD-ROM) 1997.

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Jamzad et al. "A human friendly reporting and database system for brain PET analysis" Annals of Nuclear Medicine 10(1):99-104, 1996.

Litt et al. "Graphical representation of medical information in the visual chart" Proceedings, 1994 IEEE Seventh Symposium on Computer-based Medical Systems, pp. 252-257, Jun. 11-12, 1994.

Nossister. Using Excel 5 for Windows (The User Friendly Reference), Copyright 1995, by Que Corporation.

Laurenson, R.C., "Computer Software 'Article of Manufacture' Patents," *JPTOS,*:811-824 (1995) Previously appeared in *Computer Law Reporter*, 21(6):965-974 (1995).

Miksch, Silvia, "Artificial Intelligence for Design Support: Needs Possibilities, and Limitations in ICU," 10th Postgraduate Course in Critical Care Medicine APICE '95, Springer, 1995.

Lee, Ho Sung et al., "Remote Patient Monitoring Service through World-Wide Web" Proceedings—19th International Conference—IEEE/EMBS Oct. 30- Nov. 2, Chicago, IL. USA; pp. 928-931.

Grundy, Betty L. et al., "Telemedicine in Critical Care: An Experiment in Health Care Delivery" JACEP, vol. 6, No. 10., Oct. 1977; pp. 439-444.

Andrews, Robert D. et al., "Computer Charting: An Evaluation of a Respiratory Care Computer System" *Respiratory Care*, vol. 30, No. 8, Aug. 1985; pp. 695-707.

Avila, Lorene S. and M. Michael Shabot, "Keys to the Successful Implementation of an ICU Patient Data Management System," *International Journal of Clinical Monitoring and Computing*, vol. 5, 1988, pp. 15-25.

Ayres, Stephen M. et al. Textbook of Critical Care, 3rd Edition, 1995, Harcourt Brace & Company. Sections IV & V.

Bates, David W. et al., "Reducing the Frequency of Errors in Medicine Using Information Technology" *Journal of the American Medical Informatics Association*, vol. 8, No. 4, Jul./Aug. 2001; pp. 299-308.

Berg, et al. "Remote Critical Care Consultation: Telehealth projection of clinical specialty expertise". Tripler Army Medical Center, Honolulu.

Borzo, Greg, "Web Technology, Coming to a Hospital Near You," amednews.com, The Newspaper for America's Physicians, Nov. 18, 1996, Retrieved from Internet, pp. 1-4.

Bradshaw, Karen E. et al., "Development of a Computerized Laboratory Alerting System" *Computers and Biomedical Research*, vol. 22, 1989; pp. 575-587.

Bradshaw, Karen E. et al., "Computer-Based Data Entry for Nurses in the ICU." *M. D. Computing*, vol. 6, No. 5, 1989; pp. 274-280.

Bradshaw, Karen E. et al., "Improving Efficiency and Quality in a Computerized ICU" 1988 SCAMC, Inc., pp. 763-767.

Bradshaw, Karen E. et al., "Physician Decision Making—Evaluation of Data used in a Computerized ICU" *International Journal of Clinical Monitoring and Computing*, vol. 1, 1984; pp. 81-91.

Cannon, Scott R. and Reed M. Gardner, "Experience with a Computerized Interactive Protocol System Using HELP" *Computers and Biomedical Research*, vol. 13, 1980; pp. 399-409.

Capuano, Terry Ann et al. Remote Telemetry, Nursing Management, Vo.26, No. 7, Jul. 1995, p. 26.

Chu, Wesley W. et al. "A Medical Digital Library to Support Scenario and User-Tailored Information Retrieval." *Transactions on Information Technology in Biomedicine*, vol. 4, No. 2, Jun. 2000, pp. 97-107.

Clayton, P. D. et al., "Bringing Help to the Clinical Laboratory—Use of an Expert System to Provide Automatic Interpretation of Laboratory Data" *Ann Clin Biochem*, vol. 24, Supplement, 1987; pp. S1-5 to S1-11.

Clayton, P.D. et al., "Data Driven Interpretation of Laboratory Results in the Context of a Medical Decision Support System" *Clinical Biochemistry, Principles-Methods, Applications 2*, Data Presentation Interpretation (Eds. H. Keller and Ch. Trendelenburg), Walter deGruyter, Berlin—New York, 1989; Chapter 3.7; pp. 367-380.

Clemmer, T. P. et al, "Computer Support in Critical Care Medicine" Proceedings of the Fourth Annual Symposium on Computer Applications in Medical Care, Part III, Nov. 2-5, 1980, Washington, D.C.; pp. 1557-1561.

Clemmer, Terry P. and Reed M. Gardner, "Data Gathering, Analysis, and Display in Critical Care Medicine" *Respiratory Care*, vol. 30, No. 7, Jul. 1985; pp. 586-601.

Clemmer, Terry P. and Reed M. Gardner, "Medical Informatics in the Intensive Care Unit: State of the Art 1991" *International Journal of Clinical Monitoring and Computing*, vol. 8, 1992; pp. 237-250.

DeLima, Marie et al., "Successful Implementation of a Multiple-ICU Clinical Information System in a Tertiary Care Medical Center" AMIA 2000 Annual Symposium; Session S62—Poster Session 2.

Doctors use 'remote control' to monitor ICU patients, CNN.com. technology>computing, Aug. 21, 2000, http://www.cnn.com/2000/TECH/computing/08/21/icu..t_t/.

Duncan, Ray and Jeffrey J. Pomerance, "Computer Assistance in Delivery of Patient Care in a Neonatal Intensive Care Unit," *The Use of Computers in Perinatal Medicine*, Chapter 19, Abstract only, 1982, Retrieved online from: Neonatology on the Web.

Duncan, Ray, "Computer Assisted Care in the Neonatal Intensive Care Unit," *The Use of Computers in Perinatal Medicine*, Proceedings of the 17th Annual Symposium on Computer Applications in Medical Care, American Medical Informatics Association, Abstract only, Nov. 1993, Retrieved online from: Neonatology on the Web.

East, T. D. et al., "A Strategy for Development of Computerized Critical Care Decision Support Systems," *Int J Clin Monit Comput*, vol. 8, No. 4, Abstract only, 1991-1992, Retrieved online from: PubMed.

East, Thomas D. et al., "Computers in Critical Care" *Critical Care Nursing Clinics of North America*, vol. 7, No. 2, Jun. 1995; pp. 203-216.

East, Thomas D. et al., "Development of Computerized Critical Care Protocols—A Strategy That Really Works!" Proceedings of 14th Symposium on Computer Applications in Medical Care, 1990; pp. 564-568.

East, Thomas D. et al., "Digital Electronic Communication between ICU Ventilators and Computers and Printers" *Respiratory Care*, vol. 37, No. 9, Sep. 1992; pp. 1113-1123.

East, Thomas D. et al., "Implementation Issues and Challenges for Computerized Clinical Protocols for Management of Mechanical Ventilation in ARDS Patients" SCAMC 1989: 13: 583-587.

Elliott, C. Gregory et al., "Computer-assisted Medical Direction of Respiratory Care" *Respiratory Management*, vol. 19, No. 2, 1989; pp. 31-35.

Evans, R. Scott et al., "A Computerized Approach to Monitor Prophylactic Antibiotics" 1987 SCAMC, Inc., 241-245.

Evans, R. Scott et al., "Computer Surveillance of Hospital-Acquired Infections and Antibiotic Use" *JAMA*, vol. 256, No. 8, Aug. 22/29, 1986; pp. 1007-1011.

Evans, R. Scott et al., "Development of a Computerized Adverse Drug Event Monitor" Proc Annu Symp Comput Appl Med Care. 1991; pp. 23-27.

Evans, R. Scott et al., "Development of a Computerized Infectious Disease Monitor (CIDM)" *Computers and Biomedical Research*, vol. 18, 1985; pp. 103-113.

Evans, R. Scott et al., "Prediction of Hospital Infections and Selection of Antibiotics Using and Automated Hospital Database." 1990 SCAMC, Inc.; pp. 663-667.

Evans, R. Scott et al., "Reducing the Duration of Prophylactic Antibiotic Use Through Computer Monitoring of Surgical Patients" *DICP, The Annals of Pharmacotherapy*, vol. 24, Apr. 1990; pp. 351-354.

Factor, Michael et al., "Real-Time Data Fusion in the Intensive Care Unit," *IEEE. Computer*, Abstract only, Nov. 1991, Retrieved online from: Neonatology on the Web.

Fischer, Joachim E. et al., "Quantifying Uncertainty: Physicians' Estimates of Infection in Critically Ill Neonates and Children" *CID*, vol. 38, May 15, 2004; pp. 1383-1390.

Fitzpatrick, Geraldine, "TARDIS Evaluation, Report on Final Usage Evaluation of the TARDIS Telehealth System" Distributed Systems Technology Centre, DSTC Pty. Ltd., Jul. 24, 1998; pp. 1-54.

Fleegler et al. "Apache III, Equation Update—version III-I ("eye") (Note: Includes Validation of Mortality Equations Carried Over to Version III-J)" White Paper Report, Aug. 1998, Cerner Corporation; pp. 1-13.

Fleegler et al. "Apache III, Equation Update (Version III-J)" White Paper Report, Oct. 2002, Cerner Corporation; pp. 1-22.

Frize, Monique and Robin Walker, "Clinical Decision-Support Systems for Intensive Care Units Using Case-Based Reasoning" *Med Eng Phys*, vol. 22, No. 9, 2000; pp. 671-677.

Fumai, N. et al., "Database Design of an Intensive Care Unit Patient Data Management System," *Proceedings of the Fourth Annual IEEE*

*Symposium on Computer-Based Medical Systems*, Abstract only, IEEE Computer Society Press, Los Alamitos, CA, May 12, 1991, Retrieved online from: Neonatology on the Web.

Furst, Emmanuel, "Cardiovascular Technology" *J Cardiovasc Nurs*, vol. 4, No. 1, 1989; pp. 68-78.

Galfalvy, H.C. et al., "Evaluation of Community Care Network (CCN) System in a Rural Health Care Setting" 1995 AMIA, Inc.; pp. 698-702.

Gardner, R.M, "Computers in the ICU and Surgery-Keeping Real-Time Patient Records for Decision-Making." pp. 151-157.

Gardner, Reed M, "Computerized Management of Intensive Care Patients," *M.D. Computing*, vol. 3, No. 1, Abstract only, 1986, Retrieved online from: Neonatology on the Web.

Gardner, Reed M. "Integrated Computerized Records Provide Improved Quality of Care with Little Loss of Privacy" *Journal of the American Medical Informatics Association*, vol. 1, No. 4, Jul./Aug. 1994; pp. 320-322.

Gardner, Reed M. and Karen W. Hollingsworth, "ECG and Pressure Monitoring: How to Obtain Optimal Results" The Society of Critical Care Medicine: Textbook of Critical Care, Second Edition, W.B. Saunders, Co.: Philadelphia, PA, USA, 1989; Chapter 33; pp. 295-305.

Gardner, Reed M. and M. Michael Shabot, "Computerized ICU Data Management: Pitfalls and Promises" *International Journal of Clinical Monitoring and Computing*, vol. 7, 1990; pp. 99-105.

Gardner, Reed M. and M. Michael Shabot, "Computerized ICU Data Management: Pitfalls and Promises," *International Journal of Clinical Monitoring and Computing*, vol. 7, Abstract only, 1990, Retrieved online from: Neonatology on the Web.

Gardner, Reed M. and R. Scott Evans, "Computer-Assisted Quality Assurance" *Group Practical Journal*, vol. 41, No. 3., May/Jun. 1992; pp. 8-11.

Gardner, Reed M. and Terry P. Clemmer, "Computerized Protocols Applied to Acute Patient Care" *Advances in Automated Analysis*, vol. 1, Technicon International Congress 1976, Mediad Incorporated, Tarrytown, NY; pp. 158-193.

Gardner, Reed M. and William L. Hawley, "Standardizing Communications and Networks in the ICU" Patient Monitoring and Data Management, *Managing Patient Data*, 1985 AAMI; pp. 59-63.

Gardner, Reed M. et al, "Integrated Computer Systems for Monitoring of the Critically Ill" Proc. Comput. Appl. Med. Care, 1977, pp. 301-307.

Gardner, Reed M. et al., "Assessing the Effectiveness of a Computerized Pharmacy System" Proceedings of the Fourteenth Annual Symposium on Computer Applications in Medical Care, Washington, DC, Nov. 4-7, 1990; pp. 668-672.

Gardner, Reed M. et al., "Computer-based ICU Data Acquisition as an Aid to Clinical Decision-Making" *Critical Care Medicine*, vol. 10, No. 12, Dec. 1982; pp. 823-830.

Gardner, Reed M. et al., "Computer-Critiqued Blood Ordering Using the HELP System" *Computers and Biomedical Research*, vol. 23, 1990; pp. 514-528.

Gardner, Reed M. et al., "Computerized Blood Gas Interpretation and Reporting System" *Computer Magazine*, Jan. 1975; pp. 39-45.

Gardner, Reed M. et al., "Computerized Medical Care: The HELP System at LDS Hospital" *Journal of AHIMA*, vol. 63, No. 6, 1992; pp. 68-78.

Gardner, Reed M. et al., "Computers in the Emergency Room" *Internal Medicine for the Specialist*, vol. 8, No. 3, Mar. 1987; pp. 105-114.

Gardner, Reed M. et al., "Computers in the Intensive Care Unit: A Match Meant to Be!" *Textbook of Critical Care*, Chapter 196, Third Edition, W.B. Saunders Company, 1995; pp. 1757-1770.

Gardner, Reed M. et al., "Computers in the Intensive Care Unit: Match or Mismatch?" The Society of Critical Care Medicine: Textbook of Critical Care, Second Edition, W.B. Saunders, Co.: Philadelphia, PA, USA, 1989; Chapter 26: pp. 248-259.

Gardner, Reed M. et al., "Distributed Data Base and Network for ICU Monitoring" IEEE Computers in Cardiology, Salt Lake City, Utah, Sep. 18-24, 1984; pp. 305-307.

Gardner, Reed M. et al., "Eight-Channel Data Set for Clinical EEG Transmission Over Dial-Up Telephone Network" IEEE Transactions on Biomedical Engineering, vol. BME-21, No. 3, May 1974; pp. 246-249.

Gardner, Reed M. et al., "Integrated Computer Network for Acute Patient Care" Proceedings of 1984 Symposium on Computer Applications in Medical Care, Nov. 4-7, 1984, Washington, D.C.; pp. 185-188.

Gardner, Reed M. et al., "Monitoring Direct Blood Pressure: Algorithm Enhancements" IEEE Comput Cardiol 1986;13:607-610.

Gardner, Reed M. et al., "Real Time Data Acquisition: Experience With the Medical Information Bus (MIB)" Proc Annu Symp Comput Appl Med Care. 1991; pp. 813-817.

Gardner, Reed M. et al., "The HELP Hospital Information System: Update 1998," *International Journal of Medical Informatics*, vol. 54, pp. 169-182, 1999.

Gardner, Reed M., "Computerized Alert System Use in Clinical Medicine" 1979 IEEE, pp. 136-140.

Gardner, Reed M., "Computerized Data Management and Decision Making in Critical Care" Symposium on Critical Care, *Surgical Clinics of North America*, vol. 65, No. 4, Aug. 1985; pp. 1041-1051.

Gardner, Reed M., "Computerized Intensive Care Monitoring at LDS Hospital—Progress and Development" IEEE-NIH Conference on Computers in Cardiology, Oct. 1974; pp. 97-105.

Gardner, Reed M., "Computerized Management of Intensive Care Patients" *Images, Signals and Devices*, vol. 3, No. 1, 1986; pp. 36-51.

Gardner, Reed M., "Computerized Patient Monitoring at LDS Hospital—An Evaluation" Proceedings of the San Diego Biomedical Symposium, 1971; vol. 10; pp. 151-159.

Gardner, Reed M., "Computers in Critical Care" *Wellcome Trends in Hospital Pharmacy*, Jul. 1992; p. 6-8.

Gardner, Reed M., "Computers in the ICU" *Medical Electronics*, Jun. 1984; pp. 129-135.

Gardner, Reed M., "Information Management—Hemodynamic Monitoring" *Seminars in Anesthesia*, vol. II, No. 4, Dec. 1983; pp. 287-299.

Gardner, Reed M., "Monitoring of Physiological Data in a Clinical Environment" Annual Review of Biophysics and Bioengineering, vol. 1, 1972; pp. 211-224.

Gardner, Reed M., "Patient-Monitoring Systems" Medical informatics: computer applications in health care table of contents, Chapter 12, pp. 366-399. Wesley Longman Publishing Co., Inc. Boston, MA, USA, 1990.

Gardner, Reed M., "Tomorrow's Electronic Hospital is Here Today" *IEEE Spectrum*, Jun. 1984; pp. 101-103.

Gardner, Reed M. "Performance of Computerized Protocols for the Management of Arterial Oxygenation in an Intensive Care Unit," International Journal of Clinical Monitoring and Computing 8, 1992, 271-180, Kluwer Academic Publishers, Netherlands.

Gray, J.E. et al., "Baby CareLink: Using the Internet and Telemedicine to Improve Care for High-risk Infants," *Pediatrics*, vol. 106, No. 6, Abstract only, Dec. 2000, Retrieved online from: Neonatology on the Web.

Grundy, Betty Lou et al., "Telemedicine in Critical Care: Problems in Design, Implementation, and Assessment" *Critical Care Medicine*, vol. 10, No. 7, Jul. 1982; pp. 471-475.

Halpern, Neil A. et al., "Critical Care Medicine in the United States 1985-2000: An Analysis of Bed Numbers, Use, and Costs" *Crit Care Med*, vol. 32, No. 6, 2004; pp. 1254-1259.

Haug, Peter J. et al., "Decision Support in Medicine: Examples from the HELP System" *Computers and Biomedical Research*, vol. 27, 1994: pp. 396-418.

Haug, Peter J. et al., "Hospital-Based Decision Support," *Clinical Decision Support Systems, Theory and Practice*, Springer-Verlag New York Inc., 1994; pp. 77-103.

Henderson, Susan E. et al., "Computerized Clinical Protocols in an Intensive Care Unit: How Well Are They Followed?" 1990 SCAMC, Inc.; 284-288.

Henderson, Susan et al., "Performance Evaluation of Computerized Clinical Protocols for Management of Arterial Hypoxemia in ARDS Patients" Proc. 13th Annual Symp. Comput. Appl. Med. Care. 1989. Washington, D.C., pp. 588-592.

Henderson, Susan et al., "Performance of Computerized Protocols for the Management of Arterial Oxygenation in an Intensive Care Unit" *International Journal of Clinical Monitoring and Computing*, vol. 8, 1992; pp. 271-280.

Henkind, S.J., et al., "A Clinical Alarm System Using Techniques from Artificial Intelligence and Fuzzy Set Theory," *Approximate Reasoning in Intelligent Systems, Decision and Control*, Pergamon Press, 1987, pp. 91-104.

Henkind, Steven et al. "Intensive Care Unit Monitoring Using a Real-Time Expert System," *Computers in Cardiology*, Sep. 18-21, Salt Lake City, Utah, 1994, pp. 7-12.

Heterington. "High tech meets high touch: telemedicine's contribution to patient wellness". Nursing Administration Quarterly, 22(3), Spring 1998.

Hripcsak, George et al., "Design of a Clinical Event Monitor," *Computers and Biomedical Research*, vol. 29, No. 3, Abstract only, Jun. 1996, Retrieved online from: Neonatology on the Web.

Hulse, Russell K. et al., "Computerized Medication Monitoring System" *American Journal of Hospital Pharmacy*, vol. 33, Oct. 1976; pp. 1061-1064.

Ingenerf, Josef. "Telemedicine and Terminology: Different Needs of Context Information." *Transactions on Information Technology in Biomedicine*, vol. 3, No. 2, Jun. 1999, pp. 92-100.

Janofsky, Michael, "Finding Value in Intensive Care, from Afar," The New York Times on the Web, Jul. 27, 1999, www.Visicu.com/companynews/0799_nytimes.htm.

Johnson, Bob et al., *Discern—An Integrated Prospective Decision Support System*, Symposium on Computer Applications in Medical Care. A Conference of the American Medical Informatics Associated, Nov. 5-19, 1994, Washington, D.C. p. 969.

Johnson, Dickey Seidlitz et al., "A Computerized Alert Program for Acutely Ill Patients" *Journal of Nursing Administration*, Jun. 1980; pp. 26-35.

Kaplan, Simon M. et al. Designing Support for Remote Intensive-Care Telehealth Using the Locales Framework, ACM, 1997, 99.173-184.

Kassirer, Jerome P., "The Next Transformation in the Delivery of Health Care (Editorial)," *NEJM*, vol. 332, No. 1, Abstract only, Jan. 5, 1995, Retrieved online from: Neonatology on the Web.

Keller, H. et al. Data Presentation Interpretation, Clinical Biochemistry Principles, Methods, Applications, Walter-deGruyter & Co., 1989.

Kimura, Michio et al. "MERIT-9: a patient information exchange guideline using MML, HL7, and DICOM." International Journal of Medical Informatics, vol. 51, No. 1, Jul. 1998, pp. 59-68.

Kleinholz, Lutz et al. "Supporting Cooperative Medicine: The Bermed Project." *IEEE Multimedia*, vol. 1, No. 4, Dec. 1994, pp. 44-53.

Kontaxis, K.M. et al. "Using XML and Controlled Vocabularies to Achieve Unambiguous Knowledge Acquistion From Multiple Hetereogeneous Medical Data Sources." *Information Technology Applications in Biomedicine*, 4th International IEEE EMBS Special Topic Conference on Apr. 24-26, 2003, pp. 161-164.

Kostopoulou, O. and M. Wildman, "Sources of Variability in Uncertain Medical Decisions in the ICU: a Process Tracing Study" *Qual Saf Health Care*, vol. 13, 2004; pp. 272-280.

Kuperman, Gil et al., "Continuous Quality Improvement Applied to Medical Care: Experiences at LDS Hospital" *Medical Decision Making*, vol. 11, No. 4, Oct.-Dec. 1991 Supplement; pp. S60-S65.

Kuperman, Gilad J. & Reed M. Gardner, "The Help System. A Snapshot in Time." Department of Biophysics, LDS Hospital, Salt Lake City, Utah, Sep. 1988; pp. 1-295.

Kuperman, Gilad J. et al., "Clinical Decision Support for Hospital and Critical Care" *Journal of Healthcare Information Management*, vol. 13, No. 2, Summer 1999; pp. 81-96.

Kuperman, Gilad J., Reed M. Gardner and T. Allan Pryor, "HELP: A Dynamic Hospital Information System," *Computers and Medicine*, Springer-Verlag New York Inc., 1991; 174 pages (unnumbered).

Larsen, Robert A. et al., "Improved Perioperative Antibiotic Use and Reduced Surgical Wound Infections Through Use of Computer Decision Analysis." *Infect Control Hosp Epidemiol*, vol. 10, No. 7, 1989; pp. 316-320.

Lepage, E. et al., "Development of a Computerized Knowledge Based System Integrated to a Medical Workstation: Application to Blood Transfusion" IMIA 1992; pp. 585-590.

Lepage, Eric F. et al., "Assessing the Effectiveness of a Computerized Blood Order "Consultation" System" 1992 AMIA, Inc.; pp. 33-37.

Lewis, F. John et al., "Continuous Patient Monitoring with a Small Digital Computer," *Computers and Biomedical Research*, vol. 5, Abstract only, 1972, Retrieved online from: Neonatology on the Web.

Leyerle, Beverley J. et al., "Integrated Computerized Databases for Medical Data Management Beyond the Bedside" *International Journal of Clinical Monitoring and Computing*, vol. 7, 1990, pp. 83-89.

Leyerle, Beverley J. et al., "The PDMS as a Focal Point for Distributed Patient Data." *International Journal of Clinical Monitoring and Computing*, vol. 5, 1988. pp. 155-161.

Li, Xin et al., "A World Wide Web Telemedicine System" *SPIE*, vol. 2711, 1996; pp. 427-439.

Mabry, Susan L. et al., Integrated Medical Analysis System, Proceedings of the 1997 Winter Simlation Conference, 1997, pp. 1167-1168.

Major, Kevin et al., "Wireless Clinical Alerts and Patient Outcomes in the Surgical Intensive Care Unit." *The American Surgeon*, vol. 68, Dec. 2002; pp. 1057-1060.

McDonald, CJ, "Protocol-Based Computer Reminders, the Quality of Care and the Non-Perfectibility of Man," *The New England Journal of Medicine*, vol. 295, No. 24, Abstract only, Dec. 9, 1976, Retrieved online from: Science Library.

McDonald, Clement J. and William M Tierney, "Computer-Stored Medical Records, Their Future Role in Medical Practice," JAMA, vol. 259, No. 23, pp. 3433-3440; Jun. 17, 1988.

Merz, U. et al., "Computer-Assisted Monitoring in the Neonatal Intensive Care Unit [German]," *Klin Padiatr*, vol. 207, No. 6, Abstract only, Nov./Dec. 1995, Retrieved online from: Neonatology on the Web.

Metnitz, P.G. et al., "Computer Assisted Data Analysis in Intensive Care: the ICDEV Project—Development of a Scientific Database System for Intensive Care (Intensive Care Data Evaluation Project)" *Int J Clin Monit Comput*, vol. 12, No. 3, Abstract only, 1995, Retrieved online from: Neonatology on the Web.

Microsoft Press Computer Dictionary, Third Edition, 1997, p. 430.

Microsoft Support Document 236963 describing the functionality of the Windows 95 OS.

Miller, Randolph A. et al., "Summary Recommendation for Responsible Monitoring and Regulation of Clinical Software Systems," *Annals of Internal Medicine*, vol. 127, No. 9, pp. 842-845, Nov. 1, 1997.

Morales, A. Alfredo et al., "An Application Server Approach for Integration of Clinical Systems," *Proceedings of the AMIA 1999 Annual Symposium*, Abstract only, AMIA, 1999, Retrieved online from: Neonatology on the Web.

Mrus, Joseph M., "Getting Beyond Diagnostic Accuracy: Moving toward Approaches That Can be Used in Practice" *CID*, Editorial Commentary, vol. 38, May 15, 2004; pp. 1391-1393.

Nelson, Russell M. et al., "Computer Based Monitoring of Patients Following Cardiac Surgery" *Computers in Cardiology*, vol. 5, No. 4, Jul.-Aug. 1969; pp. 926-930.

Nenov, Valeriy et al. Remote Access to Neurosurgical ICU Physiological Data using the World Wide Web, Health Care in the Information Age, 1996, pp. 242-249.

Norris, Patrick R. et al., "Web-Based Data Integration and Annotation in the Intensive Care Unit." Proc AMIA Annu Fall Symp. 1997; pp. 794-798.

Oliver, Suzanne, "Take Two Aspirin; The Computer will Call in the Morning." *Forbes*, Mar. 14, 1994. pp. 110-111.

Palley, N. A., et al. "Programming in the Medical Real-Time Environment." *AFIPS Conference Proceedings*, vol. 37, *Fall Joint Computer Conference*, Nov. 17-19, 1970, Houston Texas. pp. 589-598.

Perednia, Douglas A. Telemedine Technology and Clinical Applications, JAMA, vol. 6, Feb. 8, 1995, p. 483.

Perlstein, Paul H. et al., "Computer Assisted Newborn Intensive Care," *Pediatrics*, vol. 57, No. 4, Abstract only, Apr. 1976, Retrieved online from: Neonatology on the Web.

Pestotnik, Stanley L. et al., "Therapeutic Antibiotic Monitoring: Surveillance Using a Computerized Expert System" *The American Journal of Medicine*, vol. 88, 1990; pp. 43-48.

Pryor, T. A. et al., "The Help System" 1982 IEEE, pp. 19-27.

Pryor, T. A. et al., "The HELP System" *Journal of Medical Systems*, vol. 7, No. 2, 1983; pp. 87-102.

Pryor, T. Allan et al., "A Distributed Processing System for Patient Management" 1978 IEEE, *Computers in Cardiology*, Sep. 1978; pp. 325-328.

Pryor, T. Allan et al., "Computer System for Research and Clinical Application to Medicine" Fall Joint Computer Conference, 1968; Reprinted from AFIPS—Conference Proceedings, vol. 33, 1968; pp. 809-816.

Pryor, T. Allan et al., "HELP—A Hospital—Wide System for Computer-Based Support of Decision-Making" pp. 1-14 (unnumbered).

Pryor, T. Allan et al., "HELP—A Total Hospital Information System" Proceedings of the Fourth Annual Symposium on Computer Applications in Medical Care, Part I, Nov. 2-5, 1980, Washington, D.C.; pp. 3-7.

PTO Decision on Re-examination for Patent No. 6,804,656.

Reddy, Dr. Ramana & Dr. V. "Juggy" Jagannathan, "Final Report" *Secure Collaboration for Technology for Rural Clinical Telemedicine*, Contract No. N01-LM-6-3549, Submitted by: West Virginia Research Corporation, Concurrent Engineering Research Center, West Virginia University, Morgantown, WV, Submitted to: The National Library of Medicine, Copyright © 1999 West Virginia University; pp. 1-77.

Reddy, Dr. Ramana & Dr. V. "Juggy" Jagannathan, "Phase 1 Quarterly Report, Apr. 1-Jun. 30, 1997" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Phase 1 Quarterly Report, Jan. 1-Mar. 1, 1997" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Phase 1 Quarterly Report, Sep. 1-Dec. 1, 1996" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Project Summary; Telemedicine Team" *Secure Collaboration for Technology for Rural Clinical Telemedicine*, Funded by the National Library of Medicine, Copyright © 1999 West Virginia University; Retrieved from Internet, pp. 1-12.

Remote Monitoring of ICU Patients Lowers Mortality Rates, Complications, Johns Hopkins Newsrelease, Mar. 20, 2001, http://www.newswise.com/areticles/2001/3/ICU.JHM.html.

Reddy, S. et al., "Experiences with ARTEMIS—An Internet-Based Telemedicine System" 1997 AMIA, Inc.; pp. 759-763.

Rind, David M. et al., "Designing Studies of Computer-Based Alerts and Reminders," *M.D. Computing*, vol. 12, No. 2, Abstract only, 1995, Retrieved online from: Neonatology on the Web.

Rind, David M., et al., "Effect of Computer-Based Alerts on the Treatment and Outcomes of Hospitalized Patients," *Archives of Internal Medicine*, Vo. 154, Jul. 11, 1994, pp. 1511-1517.

Rocha, Beatriz H.S.C. et al., "Computerized Detection of Nosocomial Infections in Newborns," In Symposium on Computer Applications in Medical Care, Nov. 5-9, 1994, Washington, DC; pp. 684-688.

Rosenfeld, M.D., Brian A. FCCM, FCCP, et al., Intensive care unit telemedicine: Alternate paradigm for providing continuous intensivist care, Critical Care Medicine, vol. 28, No. 12, 2000 p. 3925.

Safran, Charles et al., "Computer-Based Support for Clinical Decision Making," *M.D. Computing*, vol. 7, No. 5, Abstract only, 1990, Retrieved online from: Neonatology on the Web.

Seiver, Adam, "ICU Bedside Technology, Critical Care Computing, Past, Present, and Future" *Critical Care Clinics*, vol. 16, No. 4, Oct. 2000; pp. 1-17. Retrieved from Internet on Oct. 13, 2003.

Shabot, M. M. et al., "Decision Support Alerts for Clinical Laboratory and Blood Gas Data" *International Journal of Clinical Monitoring and Computing*, vol. 7, 1990, pp. 27-31.

Shabot, M. Michael & Reed M. Gardner, "Decision Support Systems in Critical Care." *Computers and Medicine*, Springer-Verlag New York Inc., 1994; pp. 1-419.

Shabot, M. Michael and Mark LoBue, "Cedars-Sinai Medical Center Critical Alerting System" Cedars-Sinai Medical Center, Feb. 2004; pp. 1-16.

Shabot, M. Michael and Mark LoBue, "Real-Time Wireless Decision Support Alerts on a Palmtop PDA" 1995 AMIA, Inc., pp. 174-177.

Shabot, M. Michael et al., "Inferencing Strategies for Automated ALERTS on Critically Abnormal Laboratory and Blood Gas Data" 1989 SCAMC, Inc.; pp. 54-57.

Shabot, Michael M. et al., "Automatic Extraction of Intensity-Intervention Scores From a Computerized Surgical Intensive Care Unit Flowsheet" *The American Journal of Surgery*, vol. 154, Jul. 1987; pp. 72-78.

Shabot, Michael M. et al., "Wireless Clinical Alerts for Physiologic, Laboratory and Medication Data" Proceedings of the American Medical Informatics Association Anuual Symposium, 2000; pp. 789-793.

Shortliffe, Edward H., "Computer Programs to Support Clinical Decision Making," *JAMA*, vol. 258, No. 1, Abstract only, Jul. 3, 1987, Retrieved online from: Neonatology on the Web.

Sima, Chaoxin et al., "Vital Signs Services for Secure Telemedicine Applications" Proc AMIA Symp 1998: pp. 361-365.

Simon Project (Signal Interpretation and Monitoring), Vanderbilt University, Nashville, TN. Copyright © 2004 by Vanderbilt Universtiy, Retrieved from Internet: Page last modified Aug. 24, 2004, pp. 1-20.

Sipkoff, Martin, "Systems Aid Rural Health Delivery," Published by Premier Healthcare Resource Inc., Sep. 2003, pp. 1-4. Retrieved online from: QIPhysician.com.

Sittig, D. F. et al., "COMPAS: A Computerized Patient Advice System to Direct Ventilatory Care" Conference of Medical Informatics 88: Computers in Clinical Medicine, Institute of Measurement and Control for the British Medical Informatics Society, Nottingham, UK, Sep. 13 to 15, 1988; pp. 251-256.

Sittig, Dean F. et al., "Clinical Evaluation of Computer-Based Respiratory Care Algorithms" *International Journal of Clinical Monitoring and Computing*, vol. 7, 1990; pp. 177-185.

Sittig, Dean F. et al., "Computerized Management of Patient Care in a Complex, Controlled Clinical Trial in the Intensive Care Unit." *Computer Methods and Programs in Biomedicine*, vol. 30, 1989; pp. 77-84.

Sittig, Dean F. et al., "Computerized Screening for Identification of Adult Respiratory Distress Syndrome (ARDS) Patients" 1988 SCAMC, Inc., pp. 698-702.

Sittig, Dean F. et al., "Implementation of a Computerized Patient Advice System Using the HELP Clinical Information System" *Computers and Biomedical Research*, vol. 22, 1989; pp. 474-487.

Snowden, S. et al., "An Expert System to Assist Neonatal Intensive Care," *J Med Eng Technol*, vol. 21, No. 2, Abstract only, Mar./Apr. 1997, Retrieved online from: Neonatology on the Web.

Stewart. "Patenting of Software—Proposed Guidelines and the Magic Dividing Line that disappeared". JPTOS, pp. 681-698, Sep. 1995.

Tate, Karen E. and Reed M. Gardner, "Computers, Quality, and the Clinical Laboratory: A Look at Critical Value Reporting" Seventeenth Annual Symposium on Computer Applications in Medical Care, Oct. 30-Nov. 3, 1993, Washington D.C.; pp. 193-197.

Tate, Karen E. et al., "A Computerized Laboratory Alerting System" *M.D. Computing*, vol. 7, No. 5, 1990; pp. 296-301.

Tate, Karen E. et al., "Nurses, Pagers, and Patient-Specific Criteria: Three Keys to Improved Critical Value Reporting" 1995 AMIA, Inc.; pp. 164-168.

Thomas, Karl W. et al., "Evolution of Internet-Based Clinical Decision Support Systems," Journal of Medical Internet Research 1999; 1(2): e6 <URL: http//www.jmir.org/1999/2/e6/>, pp. 1-12.

Tobin, Martin, "Principles and Practice of Intensive Care Monitoring" McGraw-Hill, Inc., United States of America, 1998 (pp. 1-172 and pp. 1329-1407).

Tsien, Christine L., "TrendFinder: Automated Detection of Alarmable Trends", Department of Electrical Engineering and Computer Science, Massachusetts Institute of Technology, Massachusetts; Jun. 2000.

Visicu/Cerner Complaint for Patent No. 6,804,656.

Wang, Kang et al., "A Real Time Patient Monitoring System on the World Wide Web," *Proceedings of the 1996 AMIA Annual Fall Symposium*, Abstract only, Hanley and Belfus, Inc., Nov. 1996, Retrieved online from: Neonatology on the Web.

Warner, Homer R. et al., "Computer-based Monitoring of Cardiovascular Functions in Postoperative Patients" *Supplement II to Circulation*, vols. XXXVII and XXXVIII, Apr. 1968; pp. II-68 to II-74.

Weil, Max H., "Use of Automated Techniques in the Management of the Critically Ill," *Hospital Information Systems*, Marcel Dekker, Inc., 1972, 333-381.

West Virginia University Research Corporation, Secure Collaboration Technology for Rural Clinical Telemedicine: Final Report, National Library of Medicine.

Westenkow, Dwayne R., "Automating Patient Care with Closed-Loop Control," *M.D. Computing*, vol. 3, No. 2, Abstract only, 1986, Retrieved online from: Neonatology on the Web.

Whiting, R and L. Hayes, "The Practice of Telemedicine—the TARDIS Perspective" *Informatics in Healthcare—Australia*, vol. 6, No. 3, Jul./Aug. 1997; pp. 103-106.

Young, W. Hsueh-fen et al., "Computerized Ventilator Data Selection: Artifact Rejection and Data Reduction," *International Journal of Clinical Monitoring and Computing*, vol. 14, May 5, 1997: 165-176.

Transaction History (PTO Website), for U.S. Appl. No. 09/946,421, dated May 29, 2009.

Transaction History (PTO Website), for U.S. Appl. No. 09/946,304, dated May 29, 2009.

Transaction History (PTO Website), for U.S. Appl. No. 09/946,274, dated May 29, 2009.

Transaction History (PTO Website), for U.S. Appl. No. 10/985,950, dated May 29, 2009.

Transaction History (PTO Website), for U.S. Appl. No. 09/341,065, dated May 29, 2009.

Transaction History (PTO Website), for U.S. Appl. No. 90/007,927, dated May 29, 2009.

Transaction History (PTO Website), for U.S. Appl. No. 11/474,017, dated May 29, 2009.

Transaction History (PTO Website), for U.S. Appl. No. 10/355,527, dated May 29, 2009.

Transaction History (PTO Website), for U.S. Appl. No. 11/031,125, dated May 29, 2009.

Transaction History (PTO Website), for U.S. Appl. No. 09/443,072, dated May 29, 2009.

Transaction History (PTO Website), for U.S. Appl. No. 90/007,377, dated May 29, 2009.

Transaction History (PTO Website), for U.S. Appl. No. 90/008,276, dated May 29, 2009.

International Searching Authority, Notification of Transmittal of the International Search Report and the Written Opinion of the International Searching Authority, or the Declaration for Application No. PCT/IB05/00646, dated Nov. 13, 2007, 9 pages.

Supplementary European Search Report for Application No. 05708735.5, dated Nov. 13, 2008, 4 pages.

Jury Verdict in *Cerner Corporation v. Visicu, Inc.*, Civil Action No. 04-1033 (W.D. Mo., Judge Gary A. Fenner), filed Dec. 8, 2009, 5 pages.

Non-final Office Action issued in U.S. Appl. No. 11/474,017, dated Mar. 31, 2010, 35 pages.

Non-final Office Action issued in U.S. Appl. No. 10/985,950, dated May 14, 2010, 16 pages.

Non-final Office Action issued in U.S. Appl. No. 09/946,304, dated May 18, 2010, 15 pages.

"Vital Signs," http://en.wikipedia.org/wiki/Vital-signs (accessed on Jun. 9, 2010), 5 pages.

\* cited by examiner

MEDICAL INFORMATION EVENT MANAGER

FIELD OF THE INVENTION

The inventive concepts relate to network computer systems and methods. More specifically, the present invention relates to systems and methods for creating, customizing and managing events relating to medical data by healthcare professionals.

BACKGROUND

When an individual is admitted as a patient into a hospital, certain information about the patient must be acquired and made available to various members of the hospital staff. Such information includes, for example, the patient's identity, address, age and occupation, next of kin, medical history, conditions for which treatment is sought, preexisting conditions, and any medical insurance information.

During a patient's stay in a hospital, written information relating to his medical history, doctors' and nurses' observations and remarks, laboratory reports, diagnoses, doctors' orders, prescriptions and other notes by the medical team, including doctors, nurses, technicians, orderlies and the like, become part of the patient's file. Patients with chronic conditions or who are frequently hospitalized may have numerous files of substantial size which contain important historic, as well as current, information. The information that is necessary to provide a complete picture of the patient includes, for example, the patient's vital signs, fluid balance, respiratory function, blood parameters, electrocardiograms, x-rays, CT scans, MRI data, laboratory test results, diagnoses, prognoses, evaluations, admission and discharge notes, and patient registration information. This information originates from a variety of sources, including the patient, doctors, nurses, monitors connected to the patient, testing laboratories, the patient's medical records, and hospital administration records.

A massive amount of information about the patient is therefore generated in a relatively short time. Increasingly, this information is automatically recorded or manually entered into a computer-based medical information system. Critical care environments, such as hospital intensive care units, trauma units, emergency rooms and the like, are filled with state-of-the-art electronic equipment for monitoring of patients. Such systems include a plurality of patient monitoring devices that record information related to the patient's status. These systems may also capture information about the medical resources being consumed.

Furthermore, many hospitals have changed the way in which patients are billed for services. In the past, patients were typically billed on the basis of days hospitalized. With recent changes in health care management and practice, patients are now more likely to be billed on the basis of treatments received. Greater efficiency in the treatment of patients is therefore emphasized. As a consequence, hospitals now scrutinize the effect of a treatment on a patient more closely, with increased monitoring, observation and recordation of the patient's responses to treatment. The burden of entry of the increased amount of information that must be recorded about a patient has been reduced by increased automation.

Commonly owned U.S. Pat. No. 6,322,502 B1 entitled Medical Information System provides an example of a system for obtaining data and information from and about a patient in a hospital, and making it immediately and selectively accessible to various members of the medical team in a hospital in accordance with the functions performed by those members. This information may be displayed, at least in part, on screen in a flowchart. To date, systems and methods for automated use of such data and information in identifying clinic opportunities are not provided, but could be extremely useful in efficiently identifying sets of individuals as candidates for certain clinic treatments, study groups or trials. Identification of opportunities to improve patient care and efficiency of resources using automated data would also prove to be extremely beneficial.

SUMMARY OF THE INVENTION

In accordance with the present invention, a system and method are provided that assist clinicians in their research, analysis, treatment, resource utilization, and quality assurance activities. For instance, a system in accordance with the present invention may inform clinicians of patients that are suitable for clinical trials, or may inform clinicians or administrators of inefficient use of (or need for) hospital resources. Such a system utilizes information generated or provided by a medical information system to identify the occurrence of certain "events." A predefined set of condition statements that identify the occurrence of events are definable by a user (e.g., clinician) in the form of event detection processes. The occurrence of an event may, for example, cause an action to be initiated, such as messages to be generated and transmitted to bedside or remote displays of the medical information system, or to some other system. Detection of some events by one activated event detection process, may cause other event detection processes to be triggered or monitored for triggering. In one context, identification of clinical trial candidates may be performed by monitoring patients using the medical information system to gather data (e.g., "patient data"). Patient data is useful in determining whether an event has occurred. As one example, it enables an event detection process to flag a patient as a clinical trial candidate. At least some of the patient data is dynamically generated data from patient monitoring processes. The evaluation of the patient data may be performed in real-time, later off-line, or some combination thereof.

A typical medical information system in a clinic, hospital, or other medical facility may be a networked computer system that collects, stores, analyzes and manages a variety of types of patient data. Relatively static patient data, such as prior or current medical conditions, diagnosis, prognosis, statistics, and so on for one or more stays may also be maintained in the medical information system for a given patient. An account management system may be included as part of the medical information system, or it may be interfaced with the medical information system. The account management system typically stores patient account information, including patient name, address, telephone number, insurance information, billing and payment information, and the like.

Beyond relatively static patient data, dynamically changing patient data may also be collected and stored. Accordingly, monitoring processes and devices collect real-time or near real-time patient data during a patient's stay. Examples of dynamically changing patient data that may be monitored include a patient's heart rate, temperature, blood pressure, respiration rate, electrical brain activity, chemical balance or composition. These types of patient data are referred to as parameters. Many other types of patient data (or parameters) known in the art may also be collected or monitored. Monitoring is typically accomplished, to some degree, using bedside units (BSU's), which are devices included in or configured to interface with the medical information system and posted proximate to the patient. BSU's may include output devices such as display screens, printers, audible alarms, communication ports or some combination thereof, and input devices such as keypads, keyboards, input ports, probes, sensors, cameras, recorders or interfaces to other data sources.

In accordance with the present invention, an event management system is integral with or interfaced to the medical information system, which typically includes various patient monitoring systems and devices. The monitoring systems and devices provide inputs to the event management systems for determining whether or not events have occurred and event detection processes are to be triggered. The event management system may include, or may be configured for access by, any of a variety of devices, such as a desktop computer, workstation, laptop, personal digital assistant (PDA), telephone, server, or other network enabled device or programs, modules or components of such devices.

Using the event management system, event detection processes are defined by constructing a user (e.g., clinician) defined algorithm that utilizes patient data. The algorithm is comprised of a set of statements which define parameter-based tests or conditions to be met. As an example, a statement may be defined as "if temperature>100 degrees, then . . . ". Depending on the algorithm embodied in an activated event detection process, processing of patient data according to one or more event statements may cause any of several responses. That is, responses to the detection of an event may include such actions as message generation and transmission, or some other action being initiated, maintained or terminated. Messages may be sent selectively to a subset of workstations, or other devices, or may be broadcast to all workstations or devices. That is, messages may be selectively targeted to certain sets or subsets of users, classes of users, or devices. After an event is detected, the event detection process may or may not continue to be active and another event detection process (i.e., a secondary event detection process) may be triggered, in response to detection by the first event detection process.

The event management system may include an event manager module, having logic and instructions necessary for establishing a graphical user interface for user devices (e.g., a desktop computer, workstation, PDA, and so on), generating event detection process algorithms and statements, defining events and event parameters, processing inputs and outputs, and interfacing with other relevant devices and programs (e.g., operating systems, desktop applications, and so on). The event manager module may be distributed across various devices, e.g., arranged in a client-server architecture, or implemented in other manners known in the art. Preferably, the event management system generates a user interface in a Web browser context and implements commonly available and known Web browser features, such as radio buttons, toolbars, drop down lists, menus, text entry fields, graphical linking and so on.

BRIEF DESCRIPTION OF THE DRAWINGS

The drawing figures depict preferred embodiments by way of example, not by way of limitations. In the figures, like reference numerals refer to the same or similar elements. Algorithms are defined according to one or more desired events.

DETAILED DESCRIPTION OF THE PREFERRED EMBODIMENTS

A system and method in accordance with the present invention provides a means for the detection of one or more events as a function, at least in part, of information and data gathered from monitoring one or more patients. In response to the detection of an event certain actions may be taken. Event detection processes can be defined and then triggered to detect the occurrence of any of a variety of conditions. For instance, for a given clinical trial, events can be defined that indicate that a certain patient (or patients) would make a suitable candidate for that clinical trial, i.e., the patient meets necessary or desired criteria. In other cases, events can be defined that indicate that the patient is a candidate for or in need of a certain type of treatment. In yet other cases, events can be defined that indicate that hospital resources are being utilized in a certain manner. That is, such events may relate to the efficiency or inefficiency in use of certain resources, or such events may concern usage under certain circumstances. Such resources may include availability or usage of equipment, inventories, and so on. An activated event detection process determines the occurrence of such events.

In the preferred form, an event management system is used in conjunction with a medical information system, such as described in U.S. Pat. No. 6,322,502 B1. The medical information system may include or be used in conjunction with a clinical system that is used for administering clinical trials. In the preferred form, the medical information system includes bedside devices and systems (collectively "bedside units" (BSUs)) for patient monitoring and care. The medical information system provides a means for monitoring patients and collecting, storing, and maintaining patient data. Patient data may include a combination of relatively static and dynamically changing information related to a patient. Relatively static patient data may include the patient's name, address, and insurance information, as well information regarding the patient's medical history and prior care, diagnosis, prognosis, treatment and related information. Dynamically changing patient data may include a patient's heart rate, temperature, blood pressure, respiration rate, electrical brain activity, and chemical balance or composition, or other typically measured parameters.

Figure 1:
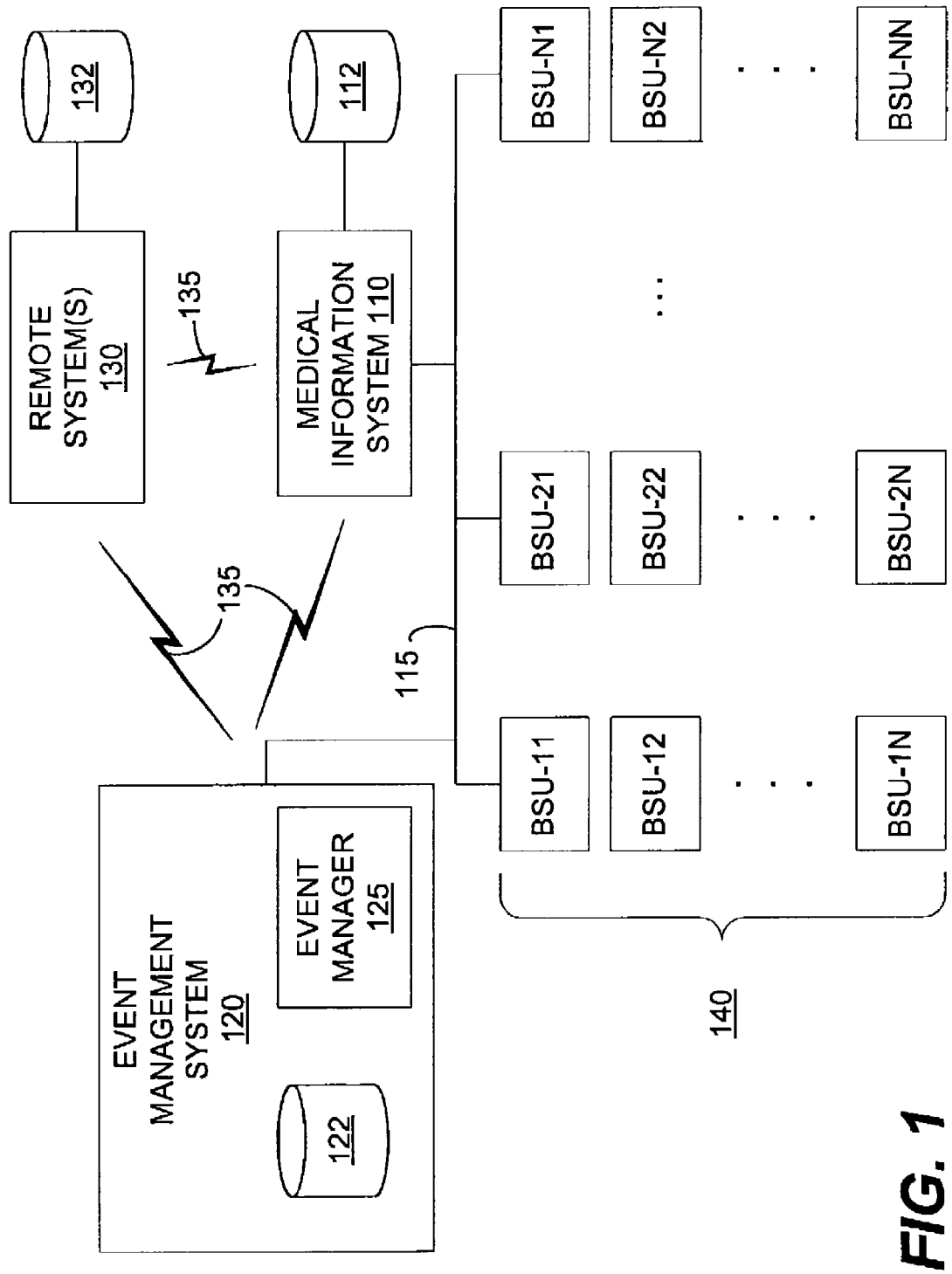
FIG. 1 is a diagram of a system architecture including an event management system in accordance with the present invention.

The present invention may be implemented within the architecture depicted in FIG. 1, as one possible embodiment. In this embodiment, a medical information system 110 comprises several workstations connected to a set of servers (not shown) via a network 115. The workstations and servers may be local, remote, or some combination thereof to each other. The medical information system 110 serves as the collector and maintainer of patient data, in a database system 112. The medical information system 110 is coupled to or includes a plurality of BSUs 140 that monitor patient status and collect patient data. In the preferred form, the BSUs also couple to network 115. Network 115 is depicted as a local area network (LAN) for simplicity. However, the present invention is not limited in this manner. Network 115 may by a LAN, wide area network (WAN), virtual private network (VPN), the Internet, World Wide Web or some combination thereof.

FIG. 1 shows an event management system 120 in accordance with the present invention, linked to medical information system 110 via network 115. There may additionally, or alternatively, be provided a wireless network link 135 between event management system 120 and medical information system 110. The event management system 120 may include its own database system 122 for storing information and data related to the events (e.g., event and statement definitions, algorithms, clinical trial treatment or resource information and data) as well as patient data. In other embodiments, the event management system 120 may be hosted on the same servers, workstations and computers as the medical information system 110 and may share at least a portion of database 112. Event management system 120 and medical information system 110 may access, or may be accessed by, one or more remote systems 130, with their own database systems 132, for data access, exchange, or maintenance. For example, such remote systems 130 may include wired or wireless computers, servers, cellular telephones, pagers, personal digital assistants, e-mail devices, or other network, Web or Internet enabled systems or devices.

In the preferred embodiment, the event management system 120 includes an event manager 125 that facilitates the creation of event detection processes and statements using a scripting language, e.g., VB Script, although other programming languages may be used. In the preferred embodiment, a statement is a VB Script function that is similar to a formula for determining the value of a given parameter or set of parameters (weighted or otherwise). A statement can call for patient data and calculate and output a parameter's value. The event manager 125 receives the outputs from statements included in the event detection process. Each executed statement returns a value, e.g., a true or false value, or initiates, terminates or maintains an action.

Figure 2A:
FIG. 2A-2B are event flow diagrams implemented by the event management system of FIG. 1.

The example of FIG. 2A illustrates a typical event 200, e.g., for inclusion in a shock study. When the variables defined in block 202 are all fulfilled simultaneously, the event management system 120 generates a message, indicated in block 204. In this case, the event 200 has occurred if a particular patient is determined to be suitable for inclusion in a study about shock. The heart rate, blood pressure, and respiration rate information may be provided by the medical information system 110 and BSUs 140.

Figure 2B:
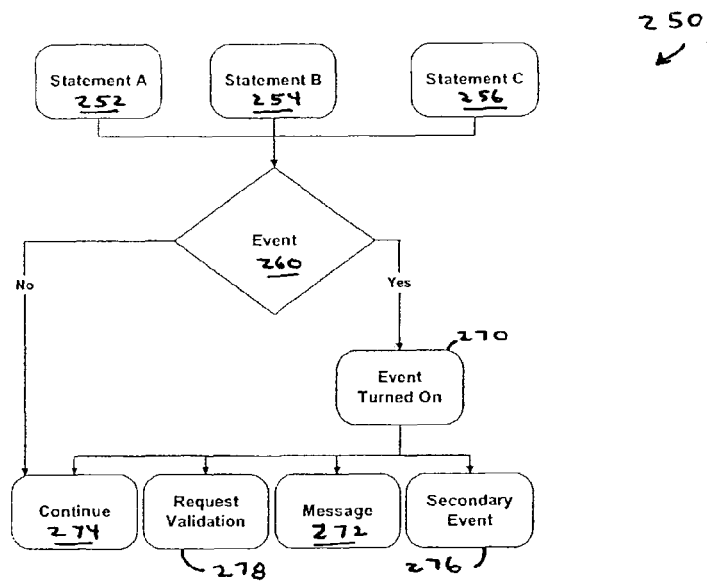

The diagram 250 of FIG. 2B offers a conceptual representation of the processing for determination of an event. In the preferred form, every event determination is based on the results of execution of one or more statements. In this example, the event includes three statements, statement A 252, statement B 254, and statement C 256. Each statement returns a numeric value into the event and the event sums all statement values. This sum is compared, in decision block 260, to predefined activation values for this event. Whenever the event value is higher than its activation value, the event has occurred or is "turned on", in step 270. When an event is detected, one or more of three actions may be taken: (1) a message may be sent, in step 272; (2) the event process may or may not continue to be active, in step 274; and (3) another, secondary event detection process may begin, in step 276. If the event is not detected, it continues to check the patient data, in step 274. In step 278, a request for validation may also be performed, wherein the user responds to or confirms the detection. For example, referring to FIG. 2A, the statement HR>120 bpm may return the value 1 when the heart rate is greater than 120 and return the value 0 when the heart rate is lower than 120.

The event manager 125 can assist clinicians in their research and quality assurance activities. An event manager graphical user interface provides users with a mechanism to define and create their own event algorithms and messages. In the preferred form, the event manager 125 runs on data from the medical information system database 112 and may be configured to operate with a time delay to enable larger amounts of data to be stored before event statement processing. When sending messages, the event manager 125 can be customized to send a message to all workstations of the event management system 120 or medical information system 110. The event manager 125 can send messages to devices (e.g., displays) within the medical information system or beyond, such that a device displaying a flowsheet for one patient could have a pop-up window rendered with a message that is not related to that flowsheet or patient.

I. Customizing with the Event Manager

Before event detection processes can be triggered in a medical information system 110, events must be created and customized to the needs and requirements of the clinical environment. Using the event manager 125, the event creation and customization process involves two main elements: creating (or customizing) statements and creating (or customizing) events. The same statement may be used in numerous events.

Event Manager Customization Screen

Figure 3:
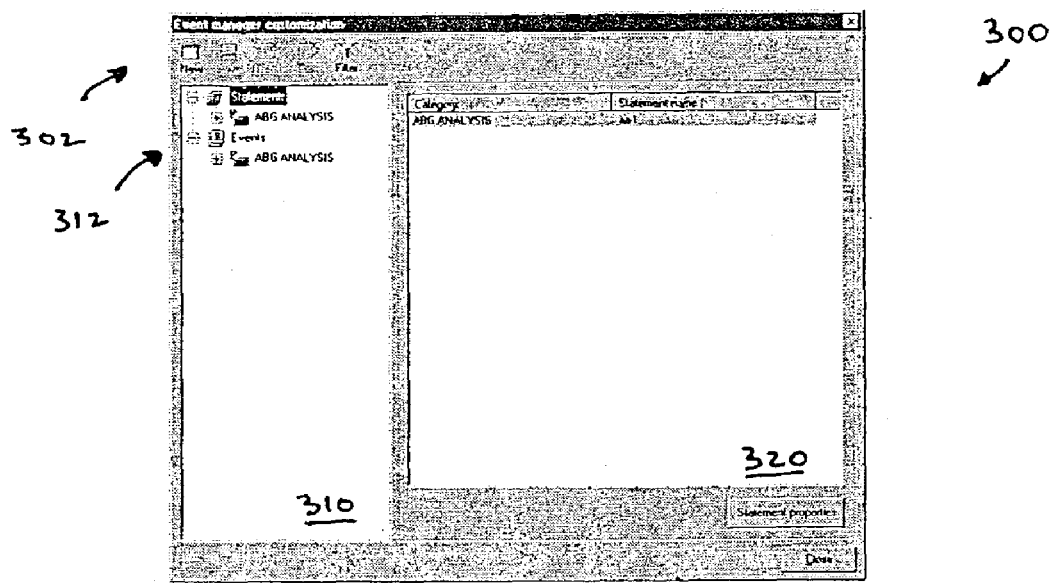
FIG. 3 is a top level event management system screen rendered on a workstation by the event management system of FIG. 1.

In the preferred form, events are created and customized using an event manager customization screen 300, shown in FIG. 3. The event manager customization screen 300 comprises an icon toolbar 302, which includes icons for creating, saving, deleting, testing, and filtering statements and events. The screen includes two panes, a statements and events pane 310 and a customization pane 320. Statements and events pane 310 includes a statements and event tree 312. The statements portion of tree 312 includes all customized statements, divided into categories. The events portion of tree 312 includes all customized event detection process divided into categories. The customization pane 320 is context sensitive and contains different functionality depending upon the element that is then being customized, namely, the statement or event detection process.

The icons in the icon toolbar 302 are context sensitive; that is, they perform different actions depending on the element being customized. The New icon facilitates creation of a new statement or event detection process, depending on whether Statement or Event is highlighted in the statements and event tree 312. The Save icon saves the newly customized statement or event detection process. The Delete icon deletes the event detection process or statement highlighted in the statements and event tree 312. The Test icon facilitates testing of event detection processes using prior data. Finally, the Filter icon facilitates the display of specific user selected statements and event detection processes.

Customizing Statements

At a top level, to customize a statement, a user may (1) open a new statement form; (2) enter a category, name, and abbreviation; (3) enter a logical script in the composition pane; (4)

select a type of return; (5) add result values; (6) check syntax; and (7) save the statement. In the preferred form, a statement is a parameter so the statement and its results may be represented in a flowsheet rendered on a medical information system 110 display. In this case, the flowsheet cell displays the resultant value of the statement, whether the event detection process including the statement was activated or not.

Figure 4A:
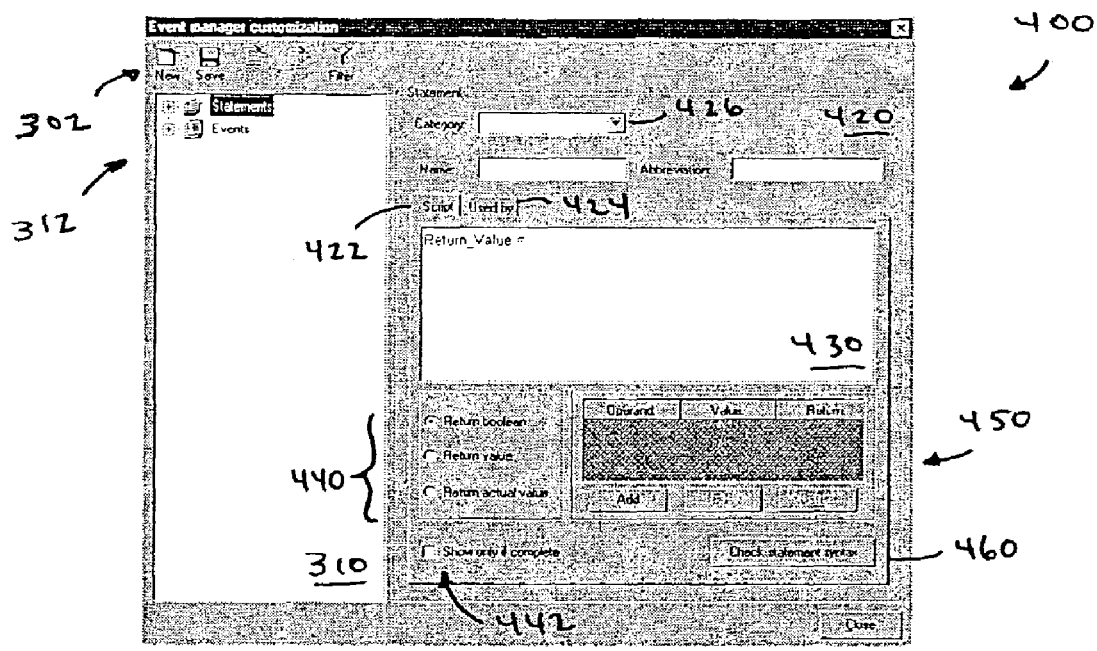
FIGS. 4A and 4B are a exemplary statement customization shots of screens, windows and forms rendered on a workstation by the event management system of FIG. 1.

At a more detailed level, statements may be built step-by-step. FIG. 4A shows a statement form (or screen) enabled from the event manager customization screen 300 shown in FIG. 3. A new statement may be created according to the following steps:

Step 1: In this step, the user opens a new (or customize) statement form 420 as follows:

1. Highlight Statements in statements and events tree 312 of screen 300.

2. Select New from the icon toolbar 302 and the statement form 420 appears in place of the customization pane 320.

3. The statement form 420 includes two tabs, which cover all stages of statement customization. A Script tab 422 is used for building a statement. A Used by tab 424 includes a list of all the event detection processes that use a selected statement. The Used by tab 424 includes data only after the statement has been used in an event detection process.

Step 2: In the second step, the user enters a category, name and abbreviation. Every statement belongs to a category, and the category is defined by a name and abbreviation. In the preferred embodiment, the statement form 420 includes a category dropdown list 426 to accept selection of a predetermined category for association with a statement. This category dropdown list 426 includes all relevant parameter categories. From the category dropdown list 426, a category may be selected. To identify the new statement, a statement name and abbreviation are entered into the relevant fields.

Step 3: In the third step, the user enters a script in composition window 430. In the preferred form, the composition window 430 is a VB Script editing window. The composition window 430 supports a high degree of functionality, such as "if/then" statements and variable definitions. For sophisticated calculations, a user may use formula parameters from its own database. In the preferred form, different script term functions appear in different colors. Delimiters appear in green, functions appear in pink, keywords appear in blue, and operators appear in dark red. Although based on VB Script, the composition window 430 may easily be used without any knowledge of VB Script. The script in the composition window always returns a value, by default; it therefore always includes a function called "Return_Value=", as is shown.

Figure 4B:
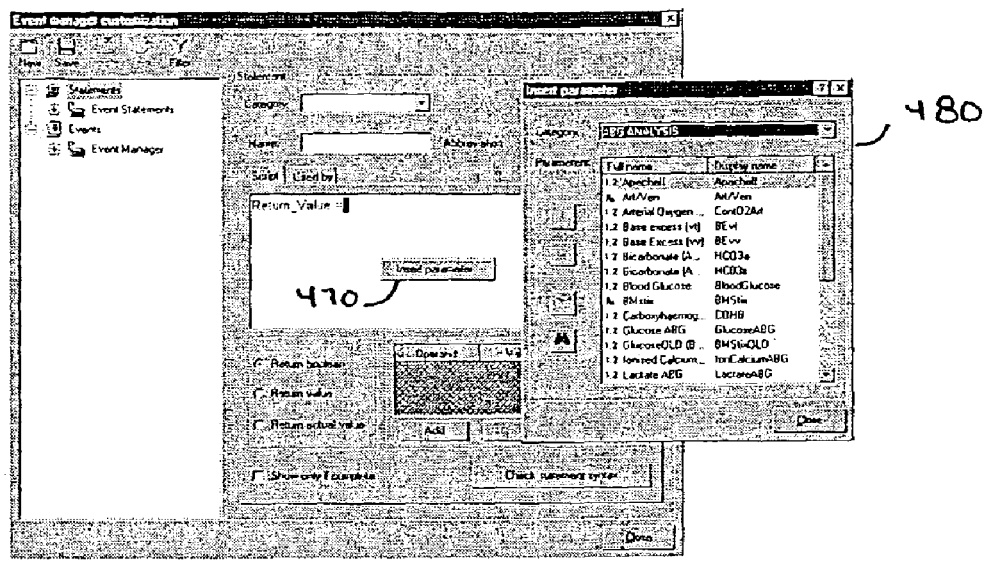

A simple script may contain only the abbreviation of the parameter to be used in the statement, for example "Return_Value=("HR")". This script will return the current heart rate value of a patient: The parameter abbreviations may be inserted into the composition window 430 using an Insert parameter function, shown in FIG. 4B. To accomplish this, a right-click action within the composition window 430 causes an Insert parameter option button 470 to be rendered. Selection of this option button 470 opens an Insert parameter form 480. The desired parameter for use in the statement can be selected from the Insert parameter form 480. Upon selection, the parameter abbreviation is automatically inserted into the composition window 430. Select Close and the Insert parameter form 480 closes. Also note, formula syntaxes may be entered into the composition window 430.

Step 4: In this step, the user selects the type of return, from the return options 440 of FIG. 4A. Each statement returns a result. The result for a given statement is used in any event detection process to which the statement is assigned. In the preferred form, this result may be one of three types:

Boolean—Returns either true or false. For example, if the heart rate is greater than 120, returns true, else returns false.

Value—Returns a predefined value for each result returned from the script. For example, if the systolic blood pressure is lower than 90, return 10, if it is between 90 and 120, return 5, and if it is greater than 120, return 7.

Actual value—Returns the actual result returned from the script. For example, if the systolic blood pressure is 90, the return result is 90.

To choose a type of return, select the appropriate radio button beside the set of return options 440. When box 442 of Show only if complete is checked, the statement will return a result value only if all the components of the statement exist. Otherwise, no result value will be returned.

Step 5: In this step, the user adds or defines result values. New statement form 420 includes mechanisms 450 to define a new result value. Selecting the Add button causes a window to open that allows selection and input of an operand. Options for editing and deleting a return value are also provided. In the preferred form, an operand dropdown list is presented from which the user can select the required operand. The dropdown list includes the following operands: $>, \geq, <, \leq, =, <>$. Once the operand is selected, the user can enter a value to which the operand refers in a provided value field, for example, >100. The user can then select the return value, as discussed above.

If working with a Boolean type of return, the returns field will contain a dropdown list with the options True or False. If choosing to return a value from a predetermined set of values, a required return value will need to be entered into a return field. If choosing to return an actual value, there is no need to define operands and return values.

Step 6: Before completion, the user can check the validity of the syntax of the new script. To do so, the user selects the Check statement syntax button 460. If the script contains any syntax errors, a message will be returned indicating the location of the error (e.g., row+column), facilitating correction of the error.

Step 7: The statement can be saved by selecting the Save icon from toolbar 302.

The above steps may be further appreciated by continuing the previous Example 1 of FIG. 2A. In creating an event to assess suitability for inclusion in a shock study, create statements for HR>120 bpm, systolic BP$\leq$90 mmHg, and respiration rate>20/m. Using screen 400, select Event manager category. Name the statement "ShockStudy_HR" and give it the abbreviation "ShockStudy_HR". In the composition window 430 enter "Return_Value=("HR")". Select the Boolean type of return and select the Show only if complete option 442. Select the operand$\geq$and enter the value 120. Select the True option in the returns dropdown list (not shown) and save the statement for HR$\geq$120 bpm. This procedure can be repeated to create statements for systolic blood pressure and respiration rate.

Customizing Events

At a top level, to customize an event: (1) open a new event form; (2) define an event detection process; (3) define action options; (4) set an event detection process schedule; and (5) save the new event detection process. Note that an event detection process may be represented as a parameter in a flowsheet. In this case, the flowsheet cell will display the result value of the event detection process, whether activated or not.

Figure 5A:
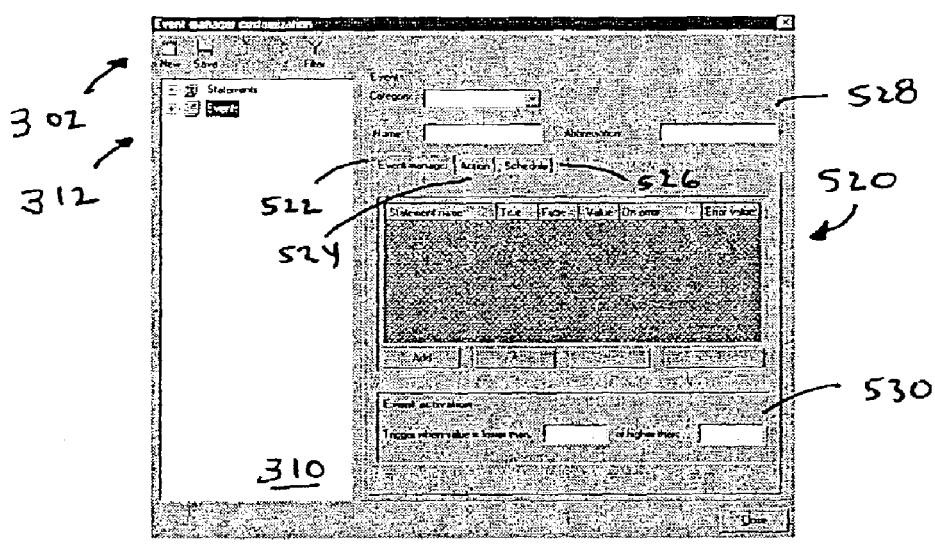
FIG. 5A-5D are exemplary event customization shots of screens, windows and forms rendered on a workstation by the event management system of FIG. 1.

At a more detailed level, event detection processes may be built step-by-step. FIG. 5A shows a new event form (or screen) enabled from the event manager customization screen 200, shown in FIG. 3. A new event detection process may be created according to the following steps:

Step 1: In this step, the user opens new event form 520 as follows:

1. In the statements and events tree 312 highlight Events.
2. In icon toolbar 302, click the New icon and the new (or customize) event form 520 appears in place of the customization pane 320. The event form 520 contains three tabs, which cover all aspects of event customization. An Event manager tab 522 is used for building the event detection process from component statements. An Action tab 524 is used to customize functions related to activation of the event detection process. A Schedule tab 526 is used to define when, how often, and for how long the event detection process will run.

Figure 5B:
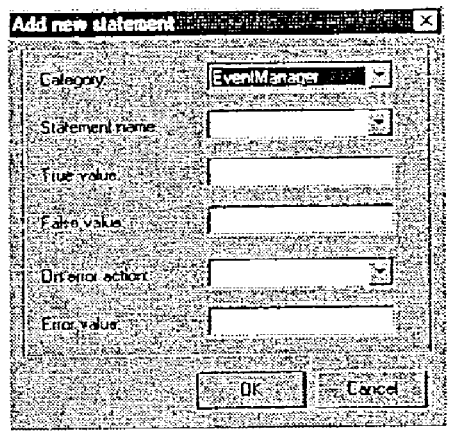

Step 2: In this step, the event detection process is defined. The statements used to define an event are selected through the Event manager tab 522. To define an event detection process, the user enters the category, name and abbreviation in the customization pane 520 fields. Like other parameters, every event detection process belongs to a parameter category, and has a name and abbreviation. The category and be chosen from a Category dropdown list. This dropdown list includes all parameter categories. Select the Add button within event form 520 and an Add new statement window 550 opens (shown in FIG. 5B).

From the Add new statement window 550, a statement category can be selected from the Category dropdown list presented in this window. From a Statement name dropdown list statements can be selected. If the type of return is Boolean, the values the statement should return for true or false results can be entered, for example, 1 for true and 0 for false. If the type of return is not Boolean, these areas will not appear. Select an action to be performed when an error condition exists from an On error action dropdown list. For example, such errors may be division by zero, not all the required values exist, and so forth. The On error action dropdown list offers two options: return value and stop process. In the return value option, once an error is identified, the statement returns a predefined value. In the stop process option, the event detection process is terminated when an error is identified in the statement. If the return value option was selected in the previous field, the error value can be entered.

Returning to the event form 520 of FIG. 5A, an Event activation area 530 is provided for entry of event detection process activation values. The Event activation area 530 is used to define the conditions under which the event detection process will be activated. Every statement returns a value to the event detection process. The values of all the statements assigned to the event detection process are added together to create the event detection value (or test condition). This value is compared to the reference values that were defined in the Event activation area 530. If the value of the event detection process is lower or higher, depending on the definition of the event detection process, then the limits that were set, the event has been detected. The event detection process results may be presented as a parameter within a flowsheet.

The above steps may be further appreciated by continuing the previous Example 1 of FIG. 2A. Wherein, after creating the statements required for the shock study event, create the event detection process, add the statements, and enter the event activation values that will enable the event detection process. From the Event area 528, select the Event Manager category and name the event "ShockStudy" and give it the abbreviation "ShockStudy" (see FIG. 5A). Add the ShockStudy_HR statement by selecting the category Event manager and selecting the name "ShockStudy_HR". Enter true value=1 and false value=0. Then select an On error action dropdown list and select a return value. Enter error value 0. Repeat for the other statements required to fully define this event, i.e., systolic blood pressure and respiration rate. Enter event test condition (e.g., "higher than 2"). In this example, if all three statements have a value of 1 (i.e., true), then the event has been detected, since the sum will be three.

Figure 5C:
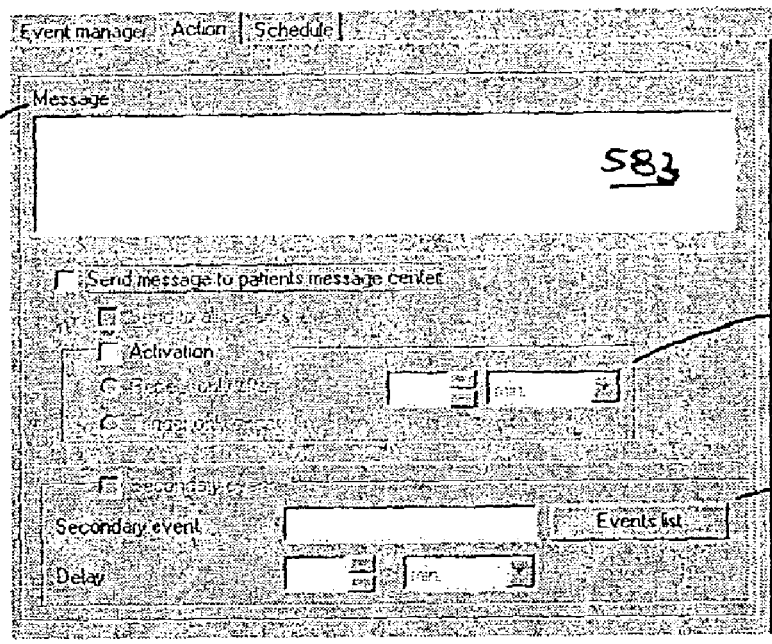

Step 3: In this step, the user defines action options. The Action tab 524 of event form 520 is used to customize actions in response to detection of an event. FIG. 5C provides an example of an Action window 580. Action window 580 is divided into three sections, representing three types of actions:

Message 582—This section allows creation and transmission control of event messages. A message field 583 defines a space for composition of a free text message that will appear when the event is detected. If a message is not to be sent, the Send message to patients message center checkbox should not be selected. If a message is to be sent to all patients, check the Send to all patients check box (shown grayed out).

Activation 584—By default, an event detection process will run according to the predefined schedule after being triggered. The Activation section 584 allows a user to define a period of time during which the event detection process will not run again after activation. In addition, a user may define that an event detection process will run only once after being triggered. To make these selections, activation of the Repeat only after button and Trigger only once button are activated (shown grayed out).

Secondary event 586—This section allows the definition of secondary event detection processes. A secondary event detection process is a process that starts when an event upon which it is dependent has been detected. For example, an event detection process that identifies low blood pressure may start another event detection process that identifies high heart rate. To select a secondary event detection process: (1) select the Events list button; an Events list window opens (not shown); (2) a category can be selected from a Category dropdown list; and (3) the required event detection process can be selected from a presented Events list. The secondary event detection process can be set to begin at a defined time after the first event is detected. This time period can be defined in minutes or hours. It is set in the Delay fields associated with the Secondary event field.

Continuing with Example 1, from Action window 580 a user can define action options for the Shock Study event, by creating a message to be sent to the patient message center once only. The text "This patient may be suitable for inclusion in shock study" may be entered into the Message field 582. The Send message to patients message center check box should be selected from Message section 582. As an example, select Trigger only once option.

Figure 5D:
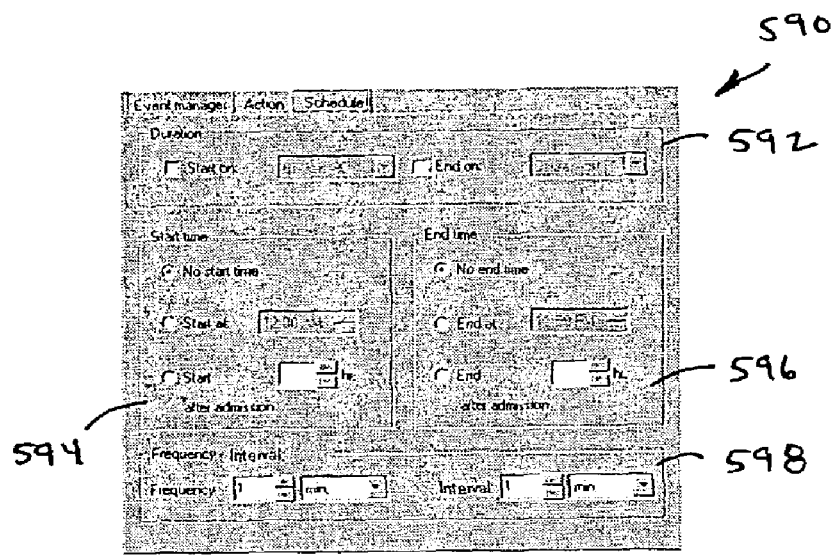

Step 4: In this step, the user can set an event detection process schedule. From event form 520, the Schedule tab 526 is selected. Selection of the Schedule tab 526 causes a Schedule window 590 to be rendered, shown in FIG. 5D. The Schedule window 590 is used for defining when and for how long the event detection process will run. The Schedule window 590 includes the following sections:

Duration 592—This section of Schedule window 590 provides mechanisms to set specific dates on which the event detection process will run.

Start time 594—This section includes three options: (1) No start time, wherein the event detection process begins to run as soon as it is assigned; (2) Start at, wherein the event detection process begins to run at a predetermined time; and (3) Start [ ] hours after admission, wherein the event detection process begins to run at some user input number of hours after the patient was admitted.

End time 596—This section includes the same functionality as the Start time 594 segment.

Frequency—Interval 598—This section provides mechanisms to set the frequency at which the event detection process will run. For example, if the user sets the Frequency field to 1 hour, the event detection process will look for values every hour. An event detection process that runs at a frequency of one minute will cause a much greater load on the system than an event detection process that runs at a frequency of one hour. Many events with a frequency of one minute running simultaneously may unacceptably slow the system, in some implementations.

The Frequency—Interval portion 598 section also provides mechanisms to set the time interval that will be checked every time the event detection process runs. For example, if a user sets the Interval field to 1 hour, every time the event detection process runs it will run on the data from the previous hour. Note, in the preferred form, the event manager 125 will always start looking for data in the first minute of the defined interval and will then continue checking forward. This means that the data used is not necessarily the most recent data available in the database. The frequency and interval should be selected according to the parameters defined in the event detection process and considering the way it will affect system performance.

An event detection process that is based on parameters that are received every minute, such as heart rate, may be set with a frequency of 1 minute. An event detection process that is based on, for example, lab data and order parameters may be set with a lower frequency, and at an interval that covers the time gaps: e.g., a frequency of 30 minutes and interval of 30 minutes. The Interval value should be selected according to the intervals on which the data is usually entered into the system. For instance, if lab data enters the system at a maximum frequency of every hour, the user may set a frequency and an interval at 1 hour. Note that if the interval is lower than the frequency, some of the data will not be searched for events. For example, if the frequency is set to 1 hour with an interval of 30 minutes, only 30 minutes of each hour will be searched by the event manager 125.

Continuing Example 1, to set an event detection process schedule using Schedule window 590, the user may select start and end times, frequency, and interval for the event detection process, so that the event detection process starts running immediately. To do so, the user selects No start time and No end time. A frequency of 1 minute is set. And, an interval of 2 minutes is set. This overlap is necessary because a value may be missing in a specific minute, or there may be a difference between the time the event is checked and the time the signal enters the system.

Step 5: In this step the event detection process is saved. Referring to FIG. 5A, to save the customized event detection process, the Save icon in icon toolbar 302 is selected. Once the event detection process is customized, it is displayed in the Used by tab 424 (see FIG. 4A) in association with the corresponding statement. A statement or event detection process that is in use in another event detection process may not be deleted.

Testing Events

Preferably, the event management system 120 includes mechanisms to test event detection processes and statements, other than those syntax related mechanisms discussed earlier. In the preferred form, the customization form enables a user to test an event detection process with existing data. Such tests help the user to estimate how often and under what circumstances the created event detection processes will be activated. This option is also available via the event manager module 125, discussed in greater detail below.

Figure 6A:
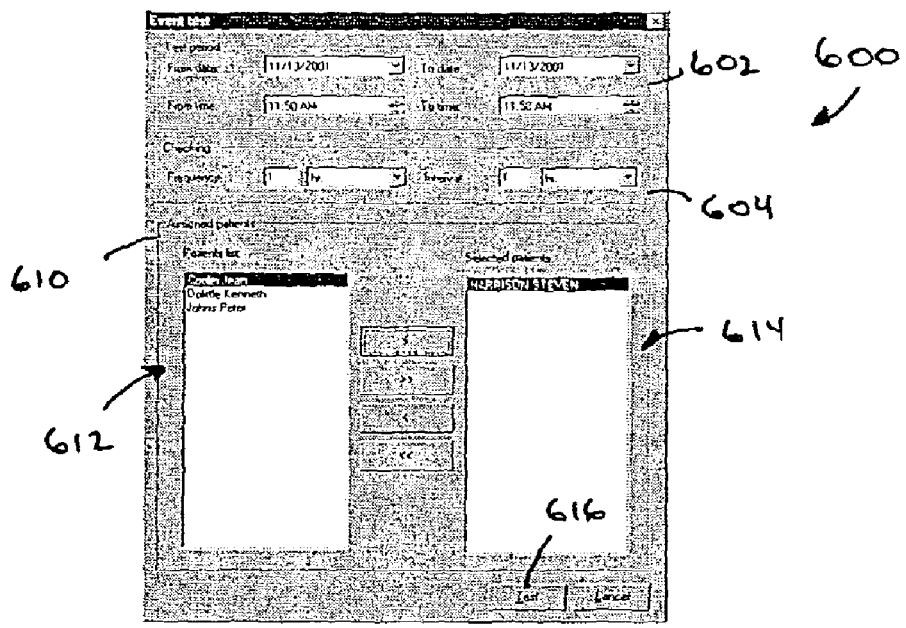
FIG. 6A-6C are exemplary event testing shots of screens, windows and forms rendered on a workstation by the event management system of FIG. 1.
Figure 6B:
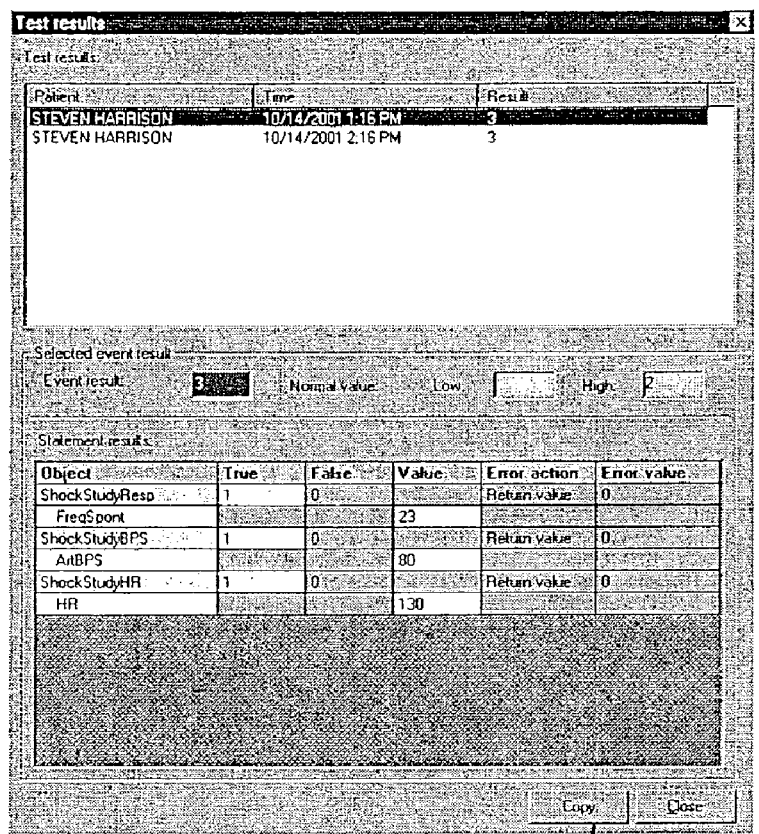

To perform a test, referring to FIG. 4A, an event detection process to be tested is selected from the statements and events tree 312. The Test icon from icon toolbar 302 is then selected, causing an Event test window 600 to open, see FIG. 6A. Required dates and times for the test are entered into the Test period section 602 of Event test window 600. Required frequency and interval are also entered in the Checking section 604. These fields have the same functions as the Frequency and Interval fields in the previously discussed Schedule window 590. A patient to be used in performance of the test is highlighted from a Patients list 612 within an Assigned patients pane 610. Highlighted patients are entered into a Selected patients list 614 using a selection arrow. A user can test the event detection process on all patients, by using the double-arrow button to move all patients to the Selected patients list 614. To initiate the test, select the Test button 616 and a Test results window 630 opens, see FIG. 6B. The duration of the test depends on the complexity of the event detection process, the defined time frame for the test, the selected frequency and the number of patients.

Figure 6C:
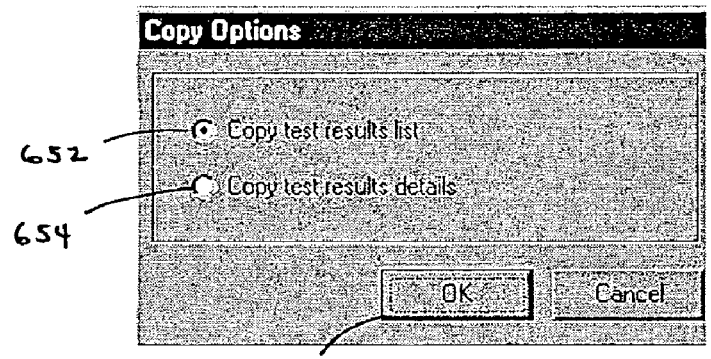

Once the test is complete, test results can be copied into another application (e.g. Microsoft Word™ or Excel™) for further analysis. To copy test results, the Copy button 632 of Test results screen 630 is selected. In the preferred form, this causes a Copy Options window 650 (see FIG. 6C) to open offering copying options, including: Copy test results list 652 or Copy test results details 654. The user selects the radio button of the preferred option. Results can be copied 'as is', or with the details of the event for each result. Selection of the OK button 656 pastes the results into the required application.

II. Using the Event Manager

Figure 7:
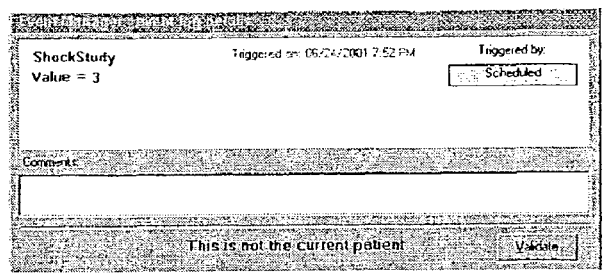
FIG. 7 is a shot of an event log rendered on a workstation by the event management system of FIG. 1.

The event manager 125 is the module that enables the user to manage existing event detection processes and view the details of events that were detected. Unlike other modules, the event manager 125 is not only related to the current patient, but can present data for all patients at any time and at any BSU. Therefore, an event message relating to one patient may be presented (or pop-up) on a display, while that display is presenting the data or flowsheet of another patient. If this is the case, the event message will preferably observe a format similar to that shown in an event manager log window 700 of FIG. 7. Note, the event manager log window 700 of FIG. 7 includes the phrase "This is not the current patient" warning at the bottom of the message pop-up dialog box, indicating that the test message relates to a patient not represented in the flowsheet.

Figure 8A:
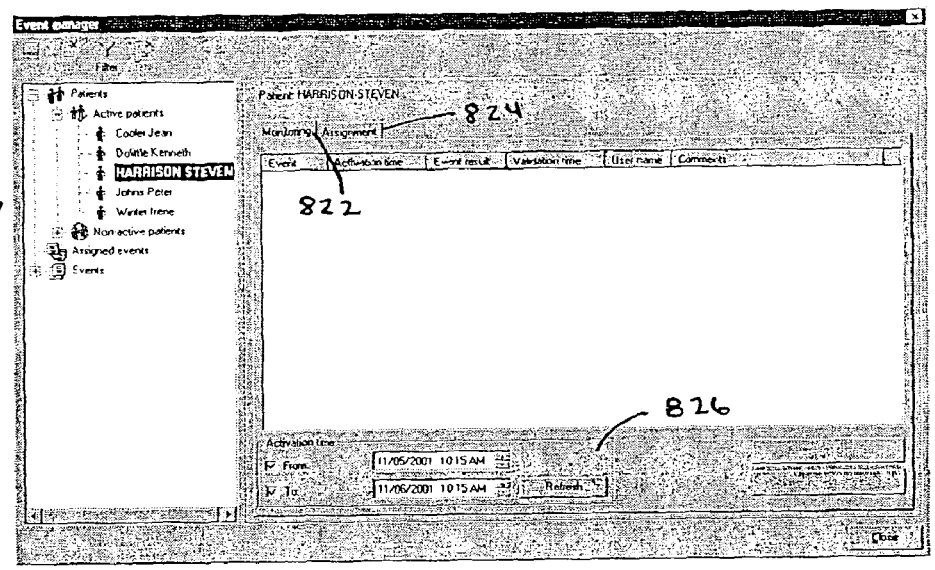
FIG. 8A-8F are exemplary event manager shots of screens, windows and forms rendered on a workstation by the event management system of FIG. 1.

FIG. 8A shows an event manager screen 800, in accordance with the present invention. The event manager screen 800 included the following elements:

Icon toolbar 802—The icon toolbar 802 facilitates access to frequently used event manager functionality. These icons are context sensitive, so are selectively enabled given the user's interactions with the various mechanisms and areas of the screen. For example, the Save button saves assignments for patients and for event detection processes.

Patients and Events Tree 812—The patients and events tree 812 includes three parts: Patients, Assigned events, and Events. The Patients portion of the tree includes two lists, i.e., Active patients and Non-active patients. The Assigned events portion includes all event detection processes that are currently assigned to patients, divided into categories. The Events portion includes all customized event detection processes, divided into categories.

Monitoring 822—The Monitoring tab 822 causes a monitoring window to be rendered that includes a list of event detection processes that have been activated, corresponding to the highlighted option in the Patients and Events tree 812 and a defined timeframe.

Assignment 824—The Assignment tab 824 causes a window to be rendered that is used for assigning event detection processes to patients and beds. The content of this window changes according to the highlighted option in the patients and events tree 812.

Figure 8B:
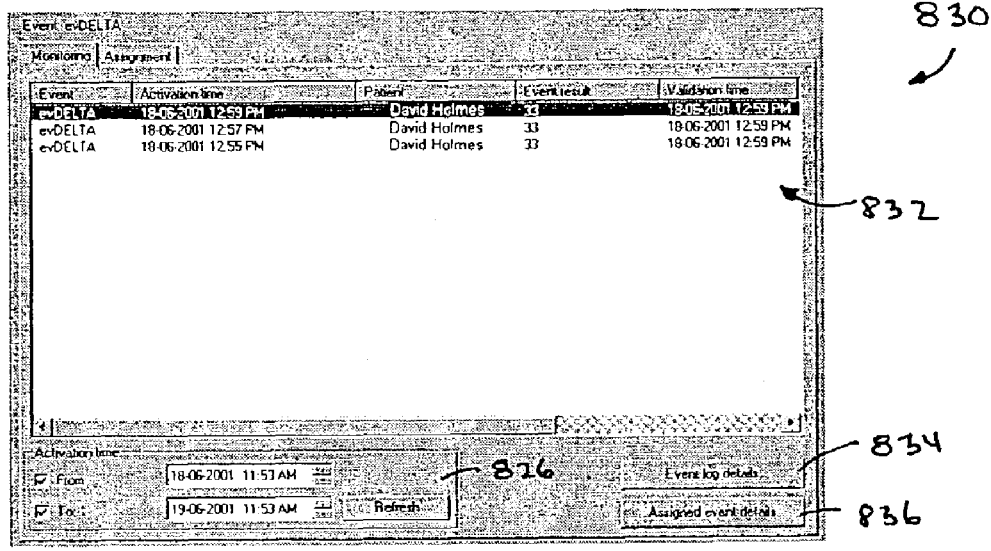

As an example, selection of the Monitoring tab 822 causes a monitoring window 830 to be rendered (see FIG. 8B). The monitoring window 830 includes a list of activated event detection processes 832, corresponding to the highlighted option in the patients and events tree 812, and a defined timeframe. The list of event detection processes changes according to the highlighted option in the patients and events tree 812. For example, if a patient name is highlighted, the list will show the event detection process activated for that patient at the specific timeframe. If an event detection process is highlighted, the list will show the activation times for the event detection process in the specific timeframe, for all patients. The timeframe for the event detection process list 832 is provided for in the Activation time section 826 of the event manager window 800. In the preferred form, the default time frame is the last 24 hours.

The Event log details button 834 of the monitoring window 830 opens a window (not shown) with activation details of the event detection process highlighted in the event detection process list 832. These details refer to a specific activation for an event detection process or for a given patient. The Assigned event details button 836 of the monitoring window 830 causes a window to be opened with activation details of the event detection process highlighted in the event detection process list 832. These details refer to general details of the event detection process.

Figure 8C:
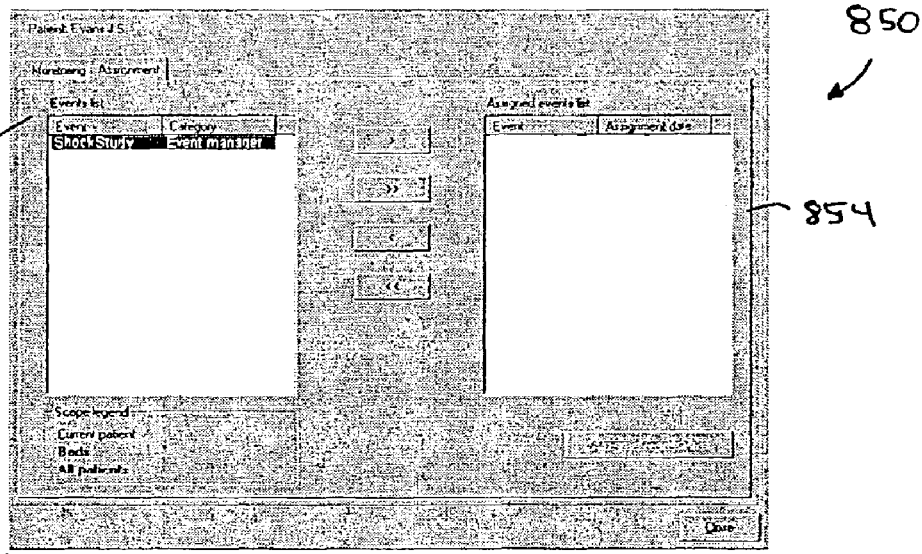

Selection of the Assignment tab 824 causes a context sensitive assignment window 850 (see FIG. 8C) to be rendered. That is, the available functions change according to the highlighted option in the patients and events tree 812. If a patient is highlighted, the assignment tab includes an Events list 852 and an Assigned events list 854. Using assignment window 850, an event detection process can be assigned to a patient as follows:

1. Highlight the required event in the Events list 852.
2. Select the arrow ">" and the event moves to the Assigned events list 854.
3. Select the Save icon in the event manager screen 800 icon toolbar 802 (see FIG. 8A).

Figure 8D:
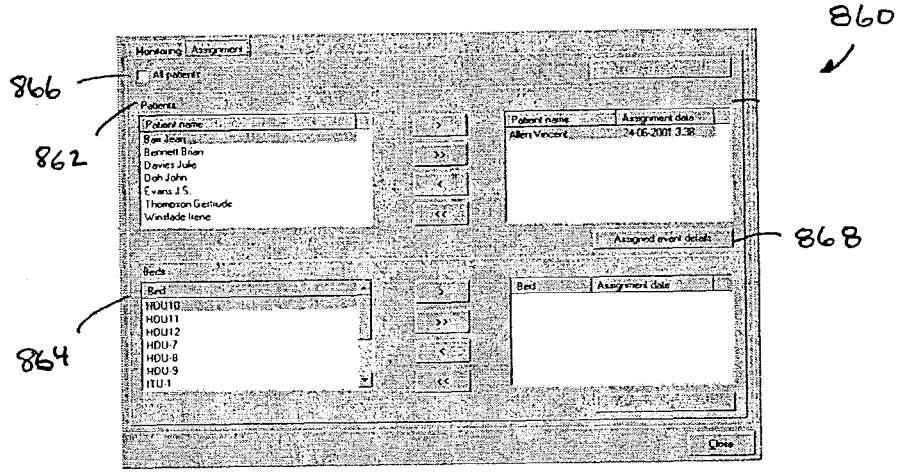

If an event detection process highlighted, the assignment window 850 is transformed to the Assignment window 860 of FIG. 8D to include a Patients list 862 and a Beds list 864. Assigning a patient or a bed to an event detection process is done in the same manner as assigning an event detection process to a patient, previously discussed, i.e., by selecting from the list and actuating the corresponding arrow button. When an event detection process is assigned to a bed, it will run on all patients that are admitted to that bed.

Figure 8E:
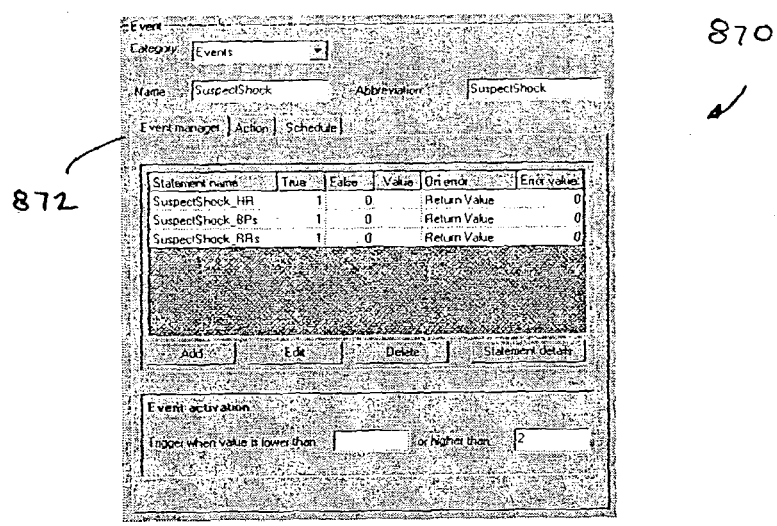
Figure 8F:
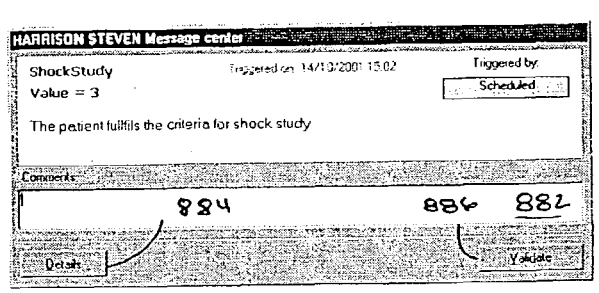

Assignment window 860 also allows a user to assign an event detection process to all patients, by selecting the All patients button 866. The Assigned event details buttons 868, associated with the assigned patients and assigned beds, are used for setting the event for the assignment. Actuation of the Assigned event details button 868 opens an assigned event details form 870 (see FIG. 8E), similar to the new event form 520 of FIG. 5A. The assigned event details form 870 includes default values assigned to the event during the customization process. The user can change these default values for the specific assignment. For instance, the user may change the frequency for a specific assignment, if assigning the event detection process to a large number of patients, in order to avoid unwanted slowdown effects on system performance. The Event manager tab 872 of the assigned event details form 870 may include an Enabled check box (not shown), which indicates that an assignment may be marked as non-active, but kept for future use. When the set of defined conditions is met, an event manager message window 880 pops up on the user's screen, such as that of FIG. 8F.

Using the event manager message window 880, a user can enter a comment in the Comments area 882 before validating the message. To see additional information regarding the event detection process, the user selects the Details button 884. The Details button 884 opens a details section (not shown) of the message window 880. In order to close the event manager message window 880, the Validate button 886 is selected. Like other validation actions in the preferred embodiment of the event manager 125, this action is registered under the name of the user who performed it.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. An event management system, configured to access or obtain patient data from a medical information system comprising a set of electronic devices including means for monitoring patients, wherein said event management system comprises:
   A. an event manager hosted, at least in part, on a set of electronic devices having output devices and input devices, said event manager comprising:
   1) a statement customizer configured to define for defining one or more statements, each of said statements configured to test at least one criterion;
   2) an event customizer, including means for defining an event detection process, selected from a plurality of event detection processes, and associating a set of said statements with said event detection process, and means for defining an event test condition, at least one event action, and a time schedule for executing said event detection process, wherein each statement of said set of statements provides information used in said event detection process;
   3) an analyzer, configured to apply said set of statements to said patient data and to determine satisfaction of said test condition, as a function of satisfaction of one or more criterion of said set of statements; and
   4) an activator, configured to initiate said at least one event action, selected from a plurality of predefined actions, in response to said satisfaction of said test condition.

2. The system of claim 1, wherein said at least one event action is the generation of a text message configured for presentation on a display of said event management system.

3. The system of claim 1, wherein said at least one event action is the generation of a test message configured for presentation on a display of said medical information system.

4. The system of claim 1, wherein at least some of said set of event electronic devices and said medical information system set of electronic devices are electronic devices shared by the event management system and the medical information system.

5. The system of claim 1, wherein said event management system is accessible by a wireless device.

6. The system of claim 1, wherein said event management system is configured to couple to said medical information system via a LAN, WAN, virtual network, private network, the world wide web, the Internet, a telephone network, or some combination thereof.

7. The system of claim 1, wherein said event customizer is configured to associate each statement from said one or more statements with more then one event detection process.

8. The system of claim 1, further comprising:
5) an event detection process tester, configured to execute said event detection process using prior patient data.

9. The system of claim 1, wherein said at least one criterion is associated with candidacy requirements for inclusion of a patient in a clinical trial and said event action includes an identification of one or more candidate patients for said clinical trial.

10. The system of claim 1, wherein said at least one criterion is associated with a medical condition of a patient and said event action includes an identification of a treatment for said medical condition.

11. The system of claim 1, wherein said at least one criterion is associated with use of one or more medical information system resources and said event action includes an identification of one or more inefficiently used resources.

12. The system of claim 1, wherein said at least one event action is transmission of a signal configured to terminate a monitoring process by said medical information system.

13. The system of claim 1, wherein said at least one event action is transmission of a signal configured to begin a monitoring process by said medical information system.

14. The system of claim 1, wherein said event customizer includes means to associate a secondary event detection process with said event detection process, wherein said secondary event detection process is chosen from a set of previously defined event detection processes.

15. The system of claim 1, wherein said event manager further includes means to set an event detection process frequency and interval for selectively enabling said analyzer.

16. The system of claim 1, wherein the time schedule comprises at least one of a frequency, an interval, a start time, an end time and a duration, for selectively enabling said analyzer.

17. An event management system, comprising:
A. a communication network;
B. a plurality of patient monitoring devices coupled to said network, including means for providing dynamically changing patient data;
C. a set of electronic devices coupled to said network and having output means and input means; and
D. an event manager, hosted on said set of electronic devices, said event manager comprising:
1) a statement customizer configured to define one or more statements, each of said statements configured to test at least one criterion;
2) an event customizer, including means for defining an event detection process, selected from a plurality of event detection processes, and associating a set of said statements with said event detection process, means for defining an event test condition, at least event action, and a time schedule for executing said event detection process, wherein each statement of said set of statements provides information that is used in said event detection process;
3) an analyzer, configured to apply said set of statements to said patient data and to determine satisfaction of said test condition, as a function of satisfaction of one or more criterion of said set of statements; and
4) an activator, configured to initiate said at least one event action, selected from a plurality of predefined actions, in response to said satisfaction of said test condition.

18. The system of claim 16, wherein said event management system is configured for access by a wireless device.

19. The system of claim 17, wherein said network includes a LAN, WAN, virtual network, private network, the world wide web, the Internet, a telephone network, or some combination thereof.

20. A method of establishing event management for use in conjunction with a medical information system, wherein said medical information system is configured for monitoring a plurality of patients and providing dynamically changing patient data, said method comprising:
A. interacting with said medical information system, including receiving said patient data;
B. defining one or more statements, each of said statements configured for testing at least one criterion;
C. defining an event detection process, selected from a plurality of event detection processes, including associating a set of said statements with said event detection process, defining an event test condition, at least one event action, and a time schedule for executing said event detection process, wherein each of the said statements provides information that is used in said event detection process;
D. establishing an analyzer configured for applying said set of statements to receive patient data and for determining satisfaction of said even test condition, as a function of satisfaction of one or more criterion of said set of statements; and
E. establishing an activator for initiating said at least one event action, selected from a plurality of predefined actions, in response to said satisfaction of said event test condition.

21. The method of claim 20, wherein said at least one event action includes generating a test message configured for presentation on a display of said event management system.

22. The method of claim 20, wherein said at least one event action includes generating a test message configured for presentation on a display of said medical information system.

23. The method of claim 20, wherein at least some of said set of event electronic devices and said medical information system set of electronic devices are electronic devices shared by the event management system and the medical information system.

24. The method of claim 20, wherein said interacting includes coupling to said medical information system via a LAN, WAN, virtual network, private network, the world wide web, the Internet, a telephone network, or some combination thereof.

25. The method of claim 20, wherein said each statement from said one or more statements can be associated with more then one event detection process of a plurality of defined event detection processes.

26. The method of claim 20, further comprising testing the event detection process by executing said event detection process using prior patient data.

27. The method of claim 20, wherein said at least one criterion is associated with candidacy requirements for inclusion of a patient in a clinical trial and said at least one event action includes an identifying one or more candidate patients for said clinical trial.

28. The method of claim 20, wherein said at least one criterion is associated with a medical condition of a patient and said at least one event action includes an identifying a treatment for said medical condition.

29. The method of claim 20, wherein said at least one criterion is associated with use of one or more medical information system resources and said at least one event action includes an identifying one or more inefficiently used resources.

30. The method of claim 20, wherein said at least one event action includes transmitting a signal configured to terminate or initiate a monitoring process by said medical information system.

31. The method of claim 20, wherein said defining an event detection process includes associating a secondary event detection process with said event, wherein said secondary event detection process is chosen from a set of previously defined event detection processes.

32. The method of claim 20, further comprising setting an event detection process frequency and interval for selectively enabling said analyzer.

33. A method of providing event management, on a computer-based system comprised of a plurality of networked electronic devices, said method comprising:

A. monitoring a plurality of patients and obtaining patient data, including dynamically changing patient data;

B. defining one or more statements, each of said statements configured for testing at least one criterion;

C. defining an event detection process, selected from a plurality of event detection processes, including associating a set of said statements with said event detection process, defining an event test condition, at least one event action, and a time schedule for executing said event detection process, wherein each statement of said set of statements provides information used in said event detection process;

D. establishing an analyzer configured for applying said set of statements to receive patient data and for determining satisfaction of said even test condition, as a function of satisfaction of one or more criterion of said set of statements;

E. establishing an activator for initiating said at least one event action, selected from a plurality of predefined actions, in response to said satisfaction of said event test condition; and F. providing an indication of said event action at one or more of said electronic devices.

34. The method of claim 33, comprising displaying a message on a display of one or more electronic devices representative of said at least one event action.

* * * * *

UNITED STATES PATENT AND TRADEMARK OFFICE
CERTIFICATE OF CORRECTION

PATENT NO. : 7,848,935 B2  
APPLICATION NO. : 10/355435  
DATED : December 7, 2010  
INVENTOR(S) : Gotlib et al.

Page 1 of 1

It is certified that error appears in the above-identified patent and that said Letters Patent is hereby corrected as shown below:

IN THE CLAIMS:

In Column 14, Line 42-43, in Claim 1, after "define" delete "for defining".

In Column 14, Line 66, in Claim 3, delete "test" and insert -- text --, therefor.

In Column 15, Line 15, in Claim 7, delete "then" and insert -- than --, therefor.

In Column 16, Line 37, in Claim 20, delete "even" and insert -- event --, therefor.

In Column 16, Line 45, in Claim 21, delete "test" and insert -- text --, therefor.

In Column 16, Line 48, in Claim 22, delete "test" and insert -- text --, therefor.

In Column 16, Line 63, in Claim 25, delete "then" and insert -- than --, therefor.

In Column 18, Line 16, in Claim 33, delete "even" and insert -- event --, therefor.

Signed and Sealed this  
Twenty-eighth Day of February, 2012

David J. Kappos  
*Director of the United States Patent and Trademark Office*